(12) United States Patent
Jupiter et al.

(10) Patent No.: US 7,412,022 B2
(45) Date of Patent: Aug. 12, 2008

(54) NON-INVASIVE STATIONARY SYSTEM FOR THREE-DIMENSIONAL IMAGING OF DENSITY FIELDS USING PERIODIC FLUX MODULATION OF COMPTON-SCATTERED GAMMAS

(76) Inventors: Clyde P. Jupiter, 265 Amberleigh Dr., Silver Spring, MD (US) 20905; Nenad N. Kondic, 210 Limona Rd., Brandon, FL (US) 33510

( * ) Notice: Subject to any disclaimer, the term of this patent is extended or adjusted under 35 U.S.C. 154(b) by 872 days.

(21) Appl. No.: 10/373,112

(22) Filed: Feb. 26, 2003

(65) Prior Publication Data

US 2003/0161526 A1    Aug. 28, 2003

Related U.S. Application Data

(60) Provisional application No. 60/360,012, filed on Feb. 28, 2002.

(51) Int. Cl.
*G01N 23/00* (2006.01)
*G01T 1/00* (2006.01)
*G01T 1/16* (2006.01)
*G01B 15/00* (2006.01)

(52) U.S. Cl. .............................. 378/2; 378/89; 378/62; 378/82; 378/87; 250/363.06

(58) Field of Classification Search ..................... 378/2, 378/63, 65, 80–82, 62, 86–89; 250/363.06
See application file for complete search history.

(56) References Cited

U.S. PATENT DOCUMENTS 3,748,470 A * 7/1973 Barrett ............................ 378/2
3,860,821 A * 1/1975 Barrett .................... 250/363.01

(Continued)

FOREIGN PATENT DOCUMENTS

DE    0118827 A2 * 11/1983

(Continued)

OTHER PUBLICATIONS

N. N. Kondic, "Density Field Determination By An External Stationary Radiation Source Using A Kernel Technique," Sym. On Measurements in Polyphase Flows—ASME Winter Annual Meeting, Dec. 10-15, 1978, pp. 1-18, San Francisco, CA, USA.

(Continued)

*Primary Examiner*—Edward J. Glick
*Assistant Examiner*—Anastasia Midkiff
(74) *Attorney, Agent, or Firm*—Doster Greene, LLC

(57) ABSTRACT

A three-dimensional image-generating device is an inspection system incorporating three components: a radiation source, a modulating unit, and a radiation detector. All three components of the inspection system may be stationary. The radiation source irradiates an external inspected object with mono-energetic gamma rays. The modulating unit, used in conjunction with the unique energy-angle characteristics of the Compton scattering process, by encoding the gamma rays, enables the identification of the spatial origin of single-scattered gamma fluxes as they pass through the inspected object enroute to the detector. The radiation detector and the computerized processor identify gamma fluxes scattered from various locations within the inspected object. The three-dimensional distribution of scattering locations within the inspected object that produce the detected single-scattered gamma fluxes and their intensity is converted to a three-dimensional mass distribution as an image within the inspected object.

83 Claims, 16 Drawing Sheets

U.S. PATENT DOCUMENTS

| | | | | |
|---|---|---|---|---|
| 3,936,639 | A | * | 2/1976 | Barrett ..................... 250/369 |
| 3,961,191 | A | * | 6/1976 | Stoner et al. .................. 378/2 |
| 4,015,135 | A | * | 3/1977 | Tipton, Jr. .................. 250/574 |
| 4,017,730 | A | * | 4/1977 | Barrett ................. 250/363.06 |
| 4,064,440 | A | * | 12/1977 | Roder ........................ 378/57 |
| 4,075,483 | A | * | 2/1978 | Tancrell et al. ......... 250/363.06 |
| 4,158,770 | A | * | 6/1979 | Davis et al. ................... 378/2 |
| 4,345,153 | A | * | 8/1982 | Yin ............................ 250/369 |
| 4,360,797 | A | * | 11/1982 | Fenimore et al. ............ 382/278 |
| 4,448,529 | A | * | 5/1984 | Krause ..................... 356/310 |
| 4,481,419 | A | * | 11/1984 | Persyk ................. 250/363.06 |
| 4,506,374 | A | * | 3/1985 | Flynn ........................... 378/2 |
| 5,173,928 | A | * | 12/1992 | Momose et al. ................ 378/4 |
| 5,512,754 | A | * | 4/1996 | Enos ....................... 250/363.1 |
| 5,717,733 | A | * | 2/1998 | Kurbatov et al. .............. 378/71 |
| 5,866,907 | A | * | 2/1999 | Drukier et al. .............. 250/366 |
| 5,960,057 | A | * | 9/1999 | Majewski et al. ............. 378/62 |
| 6,169,287 | B1 | * | 1/2001 | Warburton ............... 250/370.1 |
| 6,355,923 | B2 | * | 3/2002 | Pyyhtia et al. ........... 250/208.1 |
| 6,484,051 | B1 | * | 11/2002 | Daniel ........................ 600/436 |
| 6,510,197 | B1 | * | 1/2003 | Mitchell et al. ............... 378/62 |
| 2001/0038681 | A1 | * | 11/2001 | Stanton et al. ................ 378/55 |

OTHER PUBLICATIONS

H. Semat, "Introduction to Atomic Physics," 1947, pp. 140-145, Rinehart & Company, Inc. Publishers, New York, USA.

J.R. Lamarsh, "Introduction to Nuclear Engineering," 2d. ed., 1982, pp. 81-88, Addison-Westley Publishing Company.

* cited by examiner

FIG. 1 Measurement System 100

Eq. 15

For $n = 1$, $\sigma_{j1} = (T)\{[\Phi_{j1}(A_1'B_1' + A_1''B_1'')] + [\Phi_{j2}(A_2'B_1' + A_2''B_1'')] + \ldots + [\Phi_{jq}(A_q'B_1' + A_q''B_1'')] + \ldots + [\Phi_{jN}(A_N'B_1' + A_N''B_1'')]\}$ $\underbrace{\phantom{[\Phi_{j1}(A_1'B_1' + A_1''B_1'')]}}_{C_{j1}} \quad \underbrace{\phantom{[\Phi_{j2}(A_2'B_1' + A_2''B_1'')]}}_{C_{12}} \quad \underbrace{\phantom{[\Phi_{jq}(A_q'B_1' + A_q''B_1'')]}}_{C_{1q}} \quad \underbrace{\phantom{[\Phi_{jN}(A_N'B_1' + A_N''B_1'')]}}_{C_{1N}}$ For $n = 2$, $\sigma_{j2} = (T)\{[\Phi_{j1}(A_1'B_2' + A_1''B_2'')] + [\Phi_{j2}(A_2'B_2' + A_2''B_2'')] + \ldots + [\Phi_{jq}(A_q'B_2' + A_q''B_2'')] + \ldots + [\Phi_{jN}(A_N'B_2' + A_N''B_2'')]\}$ $\underbrace{\phantom{xxxx}}_{C_{21}} \quad \underbrace{\phantom{xxxx}}_{C_{22}} \quad \underbrace{\phantom{xxxx}}_{C_{2q}} \quad \underbrace{\phantom{xxxx}}_{C_{2N}}$ For $n = n$, $\sigma_{jn} = (T)\{[\Phi_{j1}(A_1'B_n' + A_1''B_n'')] + [\Phi_{j2}(A_2'B_n' + A_2''B_n'')] + \ldots + [\Phi_{jq}(A_q'B_n' + A_q''B_n'')] + \ldots + [\Phi_{jN}(A_N'B_n' + A_N''B_n'')]\}$ $\underbrace{\phantom{xxxx}}_{C_{n1}} \quad \underbrace{\phantom{xxxx}}_{C_{n2}} \quad \underbrace{\phantom{xxxx}}_{C_{nq}} \quad \underbrace{\phantom{xxxx}}_{C_{nN}}$ For $n = N$, $\sigma_{jN} = (T)\{[\Phi_{j1}(A_1'B_N' + A_1''B_N'')] + [\Phi_{j2}(A_2'B_N' + A_2''B_N'')] + \ldots + [\Phi_{jq}(A_q'B_N' + A_q''B_N'')] + \ldots + [\Phi_{jN}(A_N'B_N' + A_N''B_N'')]\}$ $\underbrace{\phantom{xxxx}}_{C_{N1}} \quad \underbrace{\phantom{xxxx}}_{C_{N2}} \quad \underbrace{\phantom{xxxx}}_{C_{Nq}} \quad \underbrace{\phantom{xxxx}}_{C_{NN}}$

FIG. 11

NON-INVASIVE STATIONARY SYSTEM FOR THREE-DIMENSIONAL IMAGING OF DENSITY FIELDS USING PERIODIC FLUX MODULATION OF COMPTON-SCATTERED GAMMAS

REFERENCE TO RELATED APPLICATION

This application claims priority of U.S. Provisional Patent Application Ser. No. 60/360,012, which was filed on Feb. 28, 2002. The subject matter of the earlier filed application is hereby incorporated by reference.

BACKGROUND OF THE INVENTION

1. Field of the Invention

This invention relates to systems and methods employing the encoding of scattered gamma fluxes for determining three-dimensional density distributions within an object or body to identify the presence of contraband within the object, or to identify internal characteristics within the object or body, or to detect medical abnormalities in a human body.

2. Description of the Related Art

There is a recognized and growing need for improved capability to "see" inside closed boundaries of objects and for accurate measurement of their internal characteristics. For instance, inspection devices are needed to examine baggage and containers to enhance security and search for contraband at airports, government facilities, public buildings, and other possible targets of terrorism. Inspection devices can be installed at check points to scan baggage and other types of containers so that their contents can be characterized and inspected for contraband such as explosives, weapons, drugs and other illicit substances. Non-invasive inspection devices have also become an important tool for on-line monitoring of characteristics of materials undergoing industrial processing within tanks and pipes.

In the medical field, inspection devices, especially non-invasive devices, provide many life-saving benefits. They are used by physicians and medical personnel to assist with the diagnosis and treatment of medical abnormalities in a human body and to mitigate the need for expensive and risky surgical procedures.

Imaging inspection systems have evolved from simple X-ray imaging systems providing two-dimensional images, to more sophisticated automated systems capable of three-dimensional imaging. Such current devices and techniques include Computer Assisted Tomography (CAT), Positron-Electron Emission Tomography (PET), and Magnetic Resonance Imaging (MRI). However, these conventional devices and techniques generally rely on multiple sources and/or complex arrays of detectors, and require a relative scanning motion between the inspected object and the principal system components. Such operating conditions result in significant complexity, size, cost, inspection time, and radiation exposure. A need exists for faster baggage-screening devices having good imaging capabilities to detect and identify contraband; detection machines are needed that search and accurately detect a wider range of contraband including non-metal weapons explosives and components of weapons of mass destruction; further, a need exists for cheaper and smaller inspection devices.

SUMMARY OF THE INVENTION

According to an embodiment of the invention, provided here is a three-dimensional image-generating device. The three-dimensional image-generating device includes a radiation source, a modulating unit and a radiation detector. The radiation source is configured to irradiate an object with gamma rays. The modulating unit is configured to encode gamma flux scattered from the object as the gamma rays interact with the object causing the object to generate scattered gamma rays. The modulating unit is configured to identify the spatial origin of the scattered gamma rays as the scattered gamma rays pass through the modulating unit. The radiation detector is configured to detect gamma rays scattered from within the object and passing through the modulating unit.

According to another embodiment of the invention, a measurement system is provided. The measurement system includes a modulating unit configured to receive gamma rays scattered from within an object irradiated by mono-energetic gamma rays and to modulate gamma fluxes of the scattered gamma rays with a periodic function. The modulating unit is also configured to implement an encoding process. The encoding process tags a plurality of solid angle segments of the scattered gamma flux individually with different tags. The modulation unit is further configured to encode the gamma fluxes. The encoded gamma fluxes are used in combination with the energy-angle relationship of the Compton scattering process to determine a three-dimensional distribution of local scattered gamma flux within the object.

According to another embodiment of the invention, provided is a three-dimensional image generating system including a measuring device. The measuring device is configured to identify and separate object-derived gamma fluxes originating from a plurality of isogonic slices within an object. The measuring device is configured to determine a spatial distribution of scattered gamma flux. The scattered gamma flux determination includes a magnitude of gamma fluxes of the gamma rays arriving from points located in portions of isogonic shells internal to the object and eliminates non-object derived gamma fluxes arriving from locations excluding the object.

BRIEF DESCRIPTION OF THE DRAWINGS

FIG. 11 is a system of equations (Eqs. 15) for solving a set of linear algebraic equations according to an embodiment of the invention;

DETAILED DESCRIPTION OF THE PREFERRED EMBODIMENTS

The Inspection System

Figure 1:
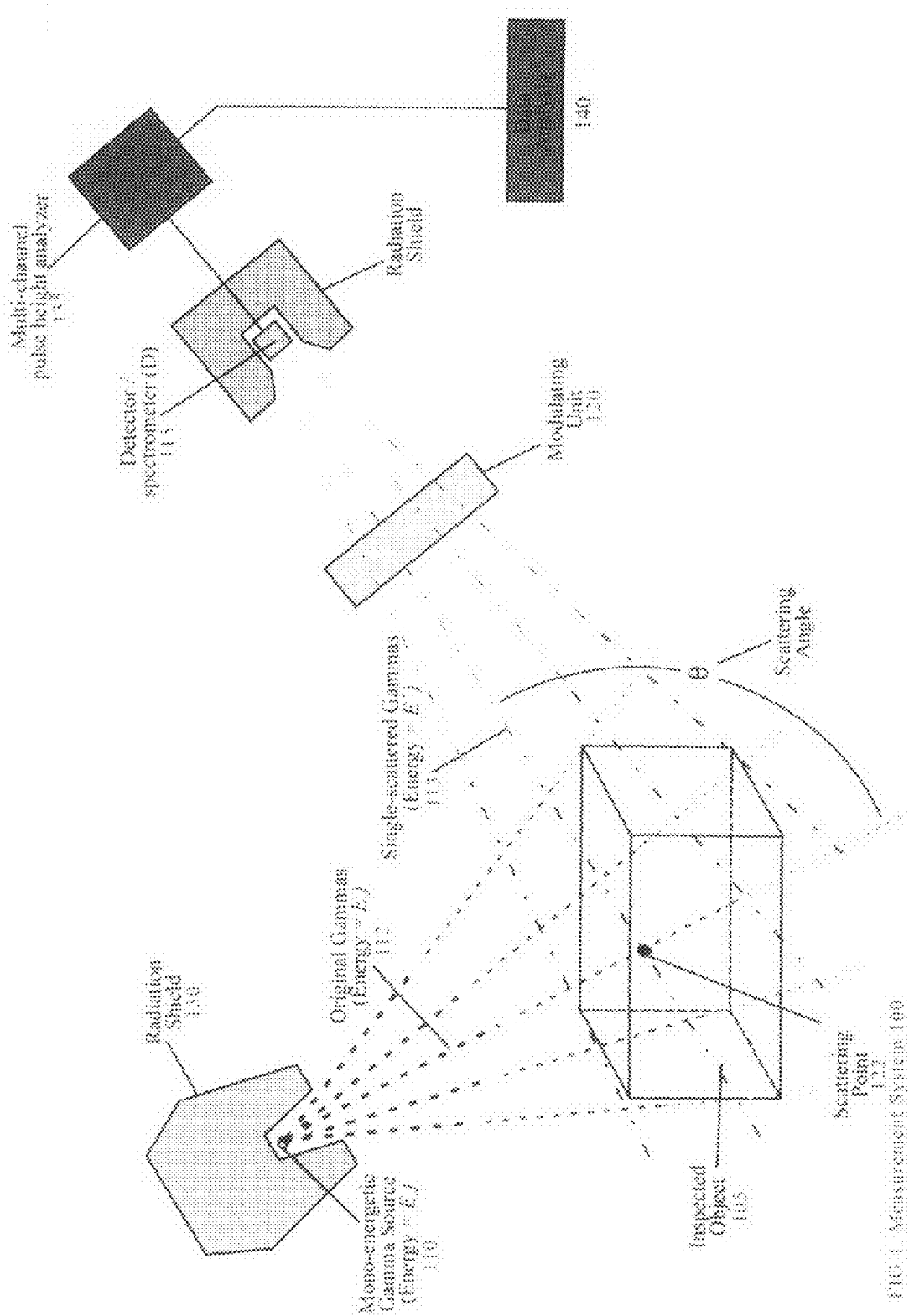
FIG. 1 depicts an inspection system according to an embodiment of the invention.

The invention, as illustrated in FIG. 1, provides a straightforward, non-invasive, rapid, and economic method for imaging an unknown volumetric density distribution within an object with opaque boundaries. The invention may be implemented by detecting and analyzing gamma rays (or X-rays) scattered from an inspected object 105, which is irradiated, for example, by a mono-energetic gamma source 110. The measurement system 100 may include a gamma radiation source 110, radiation detector 115 functioning as a gamma spectrometer, and a modulating unit 120, which may be located between inspected object 105 and detector 115, as shown, or alternately between source 110 and inspected object 105. Alternatively, the gamma radiation source 110, the radiation detector 115, and the modulating unit 120, each may be configured as a single, stationary component of the inspection system. All three of these measurement system components may also have a fixed orientation, and may be positioned on the same side or on opposite sides of the inspected object 105.

Gamma flux transmitted from the mono-energetic source 110 irradiates inspected object 105 and interacts with the object 105, which may cause a measurable fraction of scattered gammas generated within the inspected object 105 to travel from inspected object 105 to detector 115. The scattered gamma stream 113, which is the number of gamma photons passing through nodal windows within the modulator, is attenuated according to a periodic function (such as a sine or cosine function) by the modulating unit 120. This modulation acts effectively as an encoding process that tags those single-scattered gamma rays 113 that reach detector 115 after interacting with the material within the inspected object 105, or within a pre-selected region of the inspected object 105. The measurement system 100 also utilizes the energy-angle relationship of the Compton scattering process, as discussed below. This Compton energy-angle relationship, coupled with the encoding and decoding of the gamma rays scattered from inspected object 105 and passing through modulating unit 120, enables the reconstruction of the three-dimensional density distribution within inspected object 105.

One of the many features provided by the invention is the design and application of a gamma modulation unit to tag components of the areal distribution of gamma flux across any cross section of the gamma stream, after the gamma rays are scattered from inspected object 105. To enable the invention to locate scattering points within the inspected object 105, the invention may utilize the modulation unit 120 to determine the two-dimensional distribution of scattered gamma flux within inspected object 105. Conjunctively, the invention utilizes the Compton energy-angle relationship for scattered gamma rays to determine a third coordinate thereby identifying each scattering point in three-dimensional space. With the identification of all three coordinates, and measurement of the intensity of scattered gamma flux, a reconstruction of the three-dimensional gamma flux distribution and corresponding mass density distribution in inspected object 105 may be realized.

For personnel safety and to reduce background radiation, source 110 may be shielded in the lateral and rear directions by a radiation shield 130. The radiation detector 115, which may also be stationary, may record single-scattered gamma rays 113 that are projected from inspected object 105 after the original gamma rays 112 from the source interact with atoms within inspected object 105. Detector 115 is a gamma spectrometer that can register a high count rate of single detection events (i.e., single gamma photons). A multi-channel pulse height analyzer 135 (MCA) and a data analysis unit 140, sorts the detection events according to the energy of the detected gamma photon, by registering the energy spectrum of all scattered gamma photons detected by the detector 115 within a specified time period.

Modulating unit 120 imposes a periodic time-dependent attenuation on the otherwise constant incident flux of the gammas as the scattered gamma rays 113 pass through modulating unit 120 on their way to detector 115. While FIG. 1 shows the modulating unit 120 located between inspected object 105 and detector 115, in an alternative embodiment which is not shown, modulating unit 120 may be placed between source 110 and inspected object 105. In this alternate embodiment, modulating unit 120 periodically attenuates the original gamma rays from the source as the gamma rays travel toward inspected object 105. In the embodiment, as shown in FIG. 1, where modulating unit 120 is located between inspected object 105 and detector 115, the modulating unit's cross-sectional area may be oriented perpendicular to the mean direction of the gamma flux of the scattered gamma rays incident upon detector 115. Alternatively, in situations where the modulating unit 120 is positioned between radiation source 110 and inspected object 105, the modulating unit's cross-sectional area may be oriented perpendicular to the mean direction of gamma rays from source 110 incident on the inspected object 105.

Figure 6:
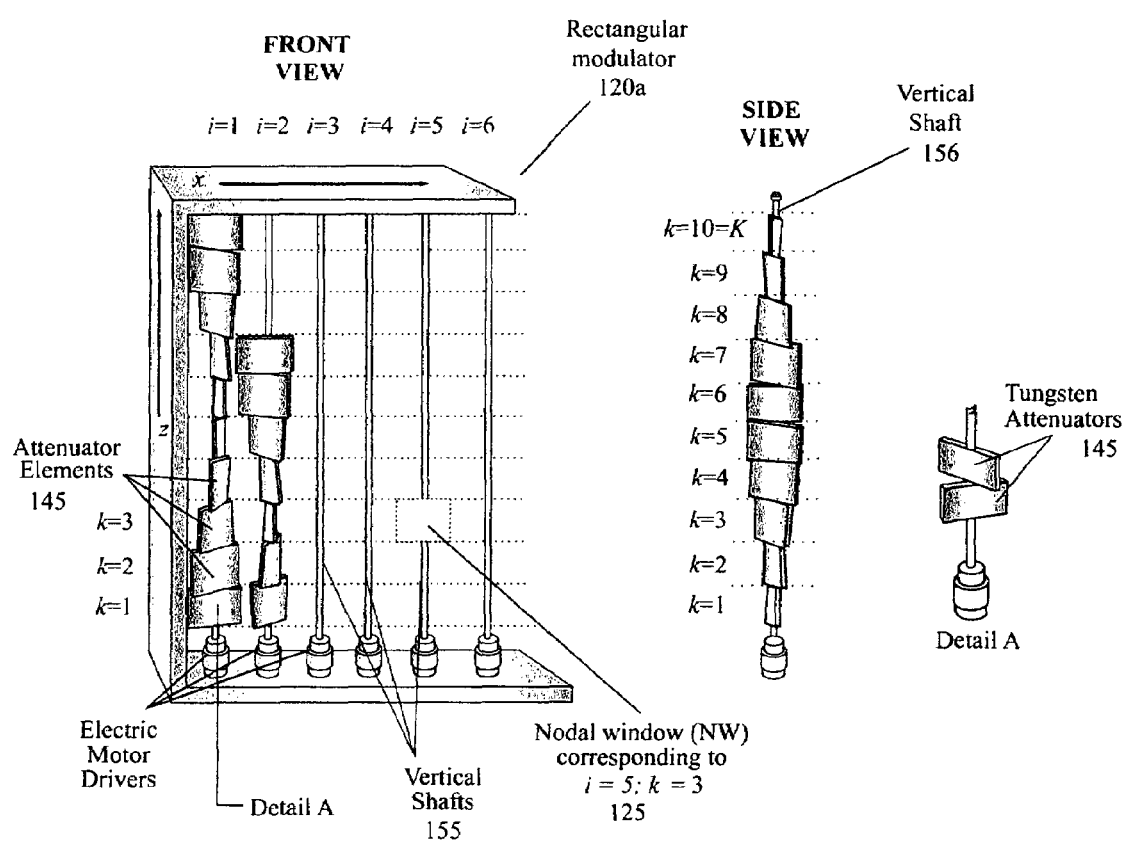
FIG. 6 depicts a rectangular modulating unit designed for rotary oscillation of rectangular gamma attenuating elements according to an embodiment of the invention.
Figure 7:
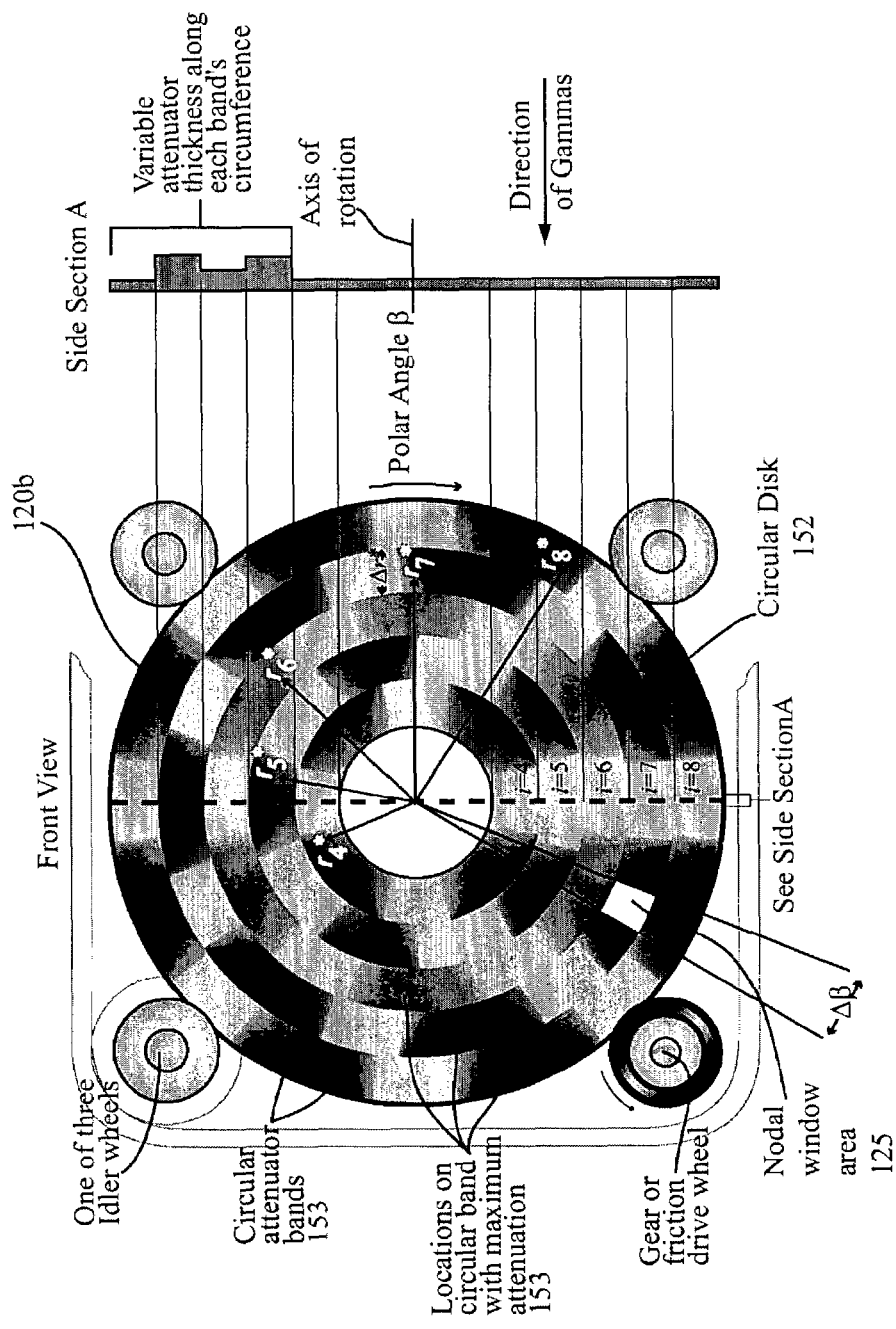
FIG. 7 illustrates a polar modulating unit including attenuator elements consisting of a circular disk with concentric circular tungsten bands of varying thickness according to an embodiment of the invention.
Figure 8:
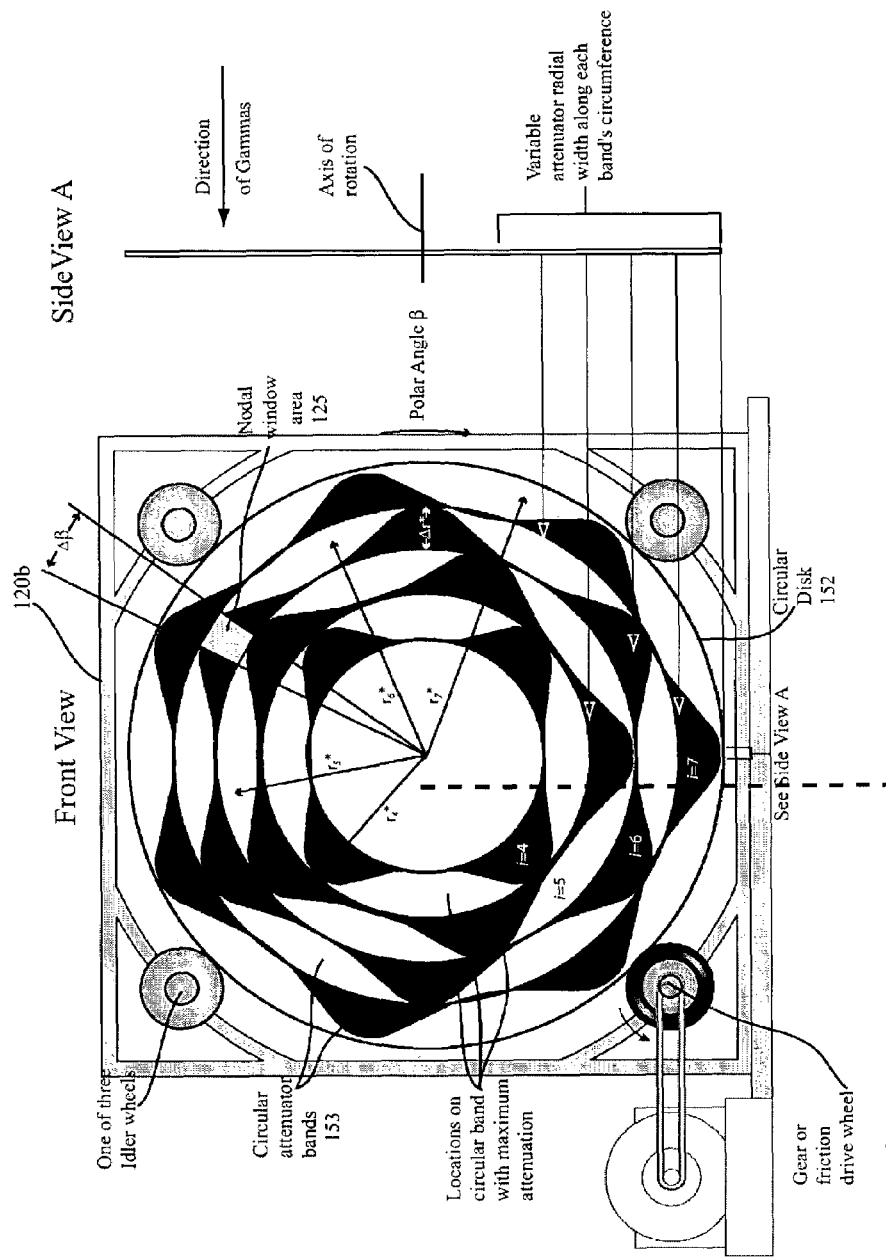
FIG. 8 illustrates a polar modulating unit including tungsten attenuator elements consisting of concentric circular bands of constant thickness and varying widths according to an alternate embodiment of the invention.

Modulating unit 120 may be further configured to include a plurality of nodal windows 125, as shown in FIGS. 6-8. As the scattered gamma rays 113 encounter the modulating unit 120 (FIG. 1) and pass through the nodal windows 125, modulating unit 120 imparts a unique time-varying attenuation on the gamma flux (i.e., gamma stream intensity) in each of the nodal windows as the scattered gamma rays exit each window 125. The time-dependent changes imposed upon the gamma flux transmission may vary with the position of each window in the areal cross-section of modulating unit 120. This time-dependent feature helps to enable a determination of the locations of the scattering points and the values of the gamma fluxes traveling from these scattering points within the corresponding sections of inspected object 105, through the modulating unit 120, and incident on the detector 115.

Dimensions of the inspection system's components, their relative positions, and processing of data can be adjusted to optimize measurements for a wide range of sizes and shapes of inspected objects.

Figure 2:
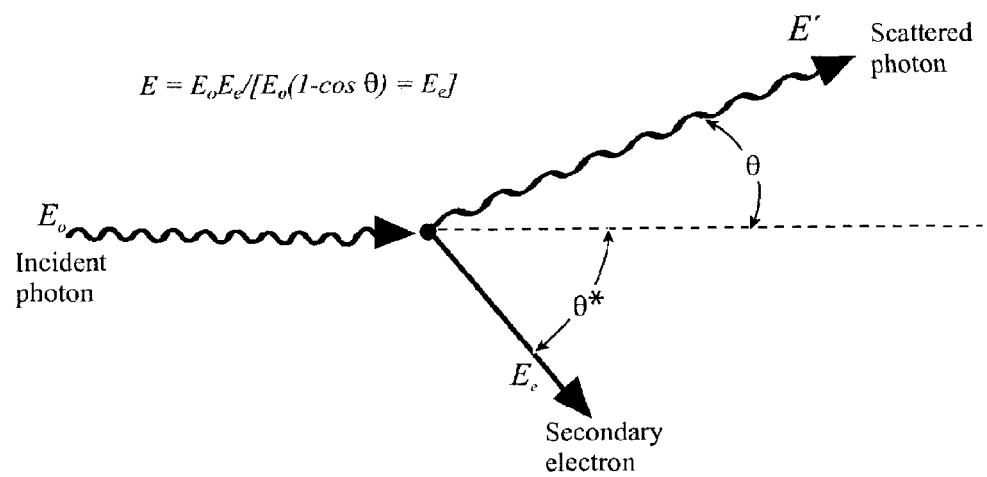
FIG. 2 shows an energy-angle relationship for Compton scattering of X-rays or gamma photons which may be employed in an embodiment of the invention.
Figure 3A:
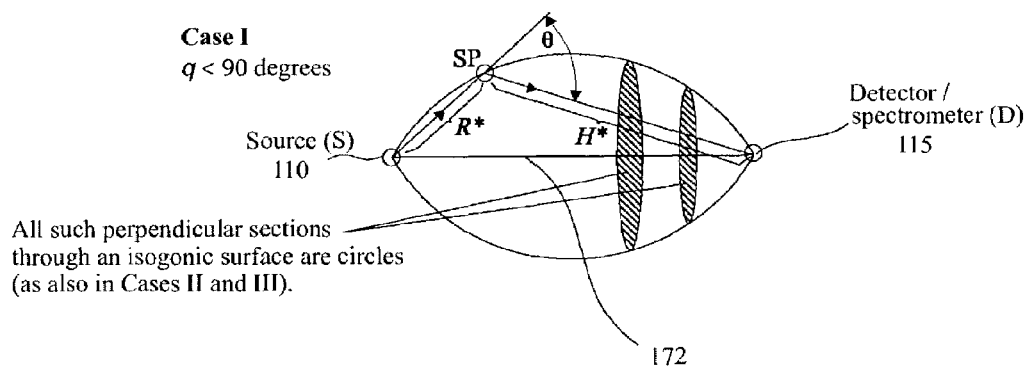
FIGS. 3A-3C illustrate configurations of isogonic surfaces and volumes which may be employed in an embodiment of the invention.
Figure 3B:
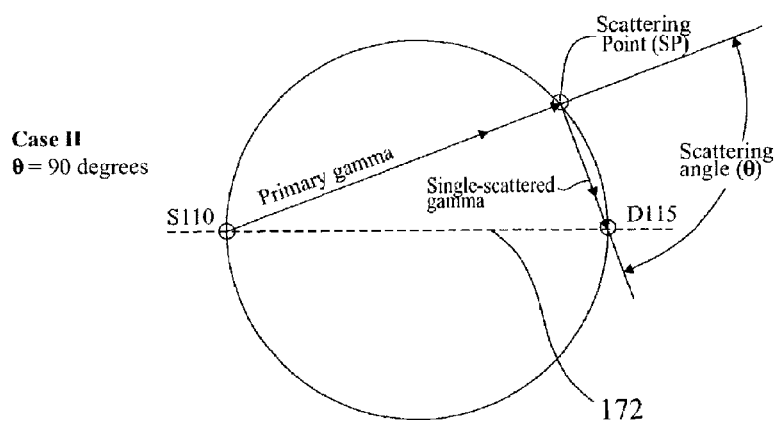
Figure 3C:
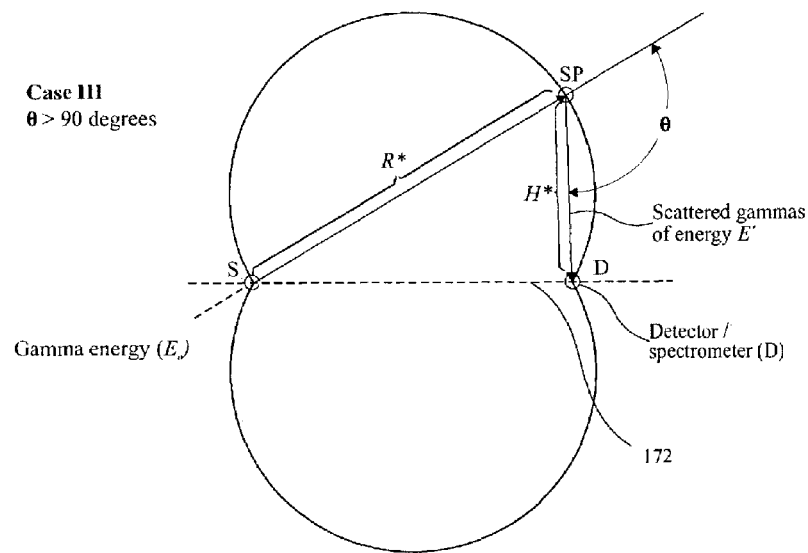

The invention provides several features and benefits. One such feature is that the invention provides a three-dimensional extension of the Compton-scattering geometry, which includes the functional and physical coupling among a gamma source, a scattering point (SP) 122 within an inspected object, and a detector. FIG. 2 illustrates the energy-angle relationship for Compton scattering of X-rays or gamma photons. Here, a primary gamma photon of energy $E_o$ interacts with an atomic electron to yield a secondary gamma photon scattered at an angle θ from the original direction and having a reduced energy E'. A secondary electron is scattered at an angle θ* to conserve momentum. The Compton energy-angle relationship for scattering of gamma photons results in a recognition that a scattering point (SP) 122 located on a circular arc passing through the source 110 and the detector 115, may be situated at any other point on that circular arc without changing the scattering angle (FIGS. 3A-3C). Rotation of this "isogonic" (equal angle) arc about the chord that connects the source 110 and the detector 115 results in a virtual isogonic surface, anywhere on which the scattering point 122 may be located and yield the same angle of scattering (and thereby, scattered photons having the same energy). The portion of these virtual surfaces within the inspected object constitutes "isogonic slices," which may be utilized in the analysis of scattered gammas and identification of their origins. The modulator unit 120 may produce a designated periodic sine or cosine time-variant attenuation of the gamma flux distribution throughout the cross-section of the gamma stream incident upon the modulator unit to encode the flux of the gamma rays in every nodal window of the modulating unit. The gamma flux encoding provided by the modulating unit 120 enables the identification of the point of origin of gamma rays, which have undergone scattering in the inspected object, and are discriminated by the detector (based upon their measured energy) from other gamma rays arriving at the detector from other isogonic slices. Utilizing gamma rays transmitted from a single mono-energetic source and measured by a single detector spectrometer, the invention also provides a method for simultaneous spatial-encoding, which may be performed by the modulating unit, and energy-encoding of Compton-scattered gamma flux traveling from the inspected object to the detector. A Fourier transform analysis may be included in the decoding process to analyze the measured detector count rates, thus enabling a determination of the three-dimensional distribution of scattering points and corresponding three-dimensional mass density distribution within a stationary inspected object irradiated by mono-energetic gammas.

As a more detailed description of the components shown in FIG. 1, the radiation source 110 can be any radioactive isotope emitting mono-energetic gammas having energies, for example, in the range of approximately a few hundred KeV to the MeV range. The radiation source 110 may be, for example, cesium-137, which emits mono-energetic gamma rays having an energy of 661 Kev or sodium-22, emitting gamma photons at 1.27 MeV. Alternatively, in addition to the use of isotopic sources, the gamma radiation source may be any generator of mono-energetic gamma photons. Radiation source 110 may be stationary and housed in a radiation shield 130. During the measurement, the radiation shield 130 may include an opening on one side to permit gamma radiation to stream out in a conical solid angle large enough to irradiate a portion or the entire inspected object 105. When selecting the strength of the source to be used in a particular application, factors such as the desired inspection time, size, density, distance, and geometry of the inspected object may be considered.

Another physical attribute that may be considered in configuring the invention is that the lateral dimensions of the radiation source may be selected to be significantly smaller in comparison to the linear dimensions of the overall inspection system and the inspected object. If, in this example, the size of the inspected object and the distance of the inspected object from the source are more than two orders of magnitude larger than the size of the radiation source, the radiation source can be approximated by a point source, which will simplify the mathematical analysis, as discussed below.

The Modulating Unit

The gamma flux modulating unit 120, as shown in FIGS. 1, 4, 6, 7, and 8, incorporates time-dependent gamma attenuators 145 placed in the path of the scattered gamma flux 113 traveling from inspected object 105 to detector 115 (or alternatively, from the radiation source 110 to inspected object 105). Each gamma attenuator 145 functions as an attenuating element of its associated nodal window 125. The modulating unit 120 is configured to encode each individual solid angle segment of the gamma flux before the gamma flux arrives at detector 115. Subsequently, the resulting signals are subjected to further processing. The encoding by modulating unit 120 provides a unique time-varying tag at any moment in real time during which the gamma rays 113 pass through the modulating unit 120. Modulating unit 120 acts upon either the original or scattered gamma rays, depending upon the location of the modulating unit, in order to encode the gamma flux and thereby assist in a simultaneous determination of the spatial origin and flux intensity of the scattered gammas.

Figure 4:
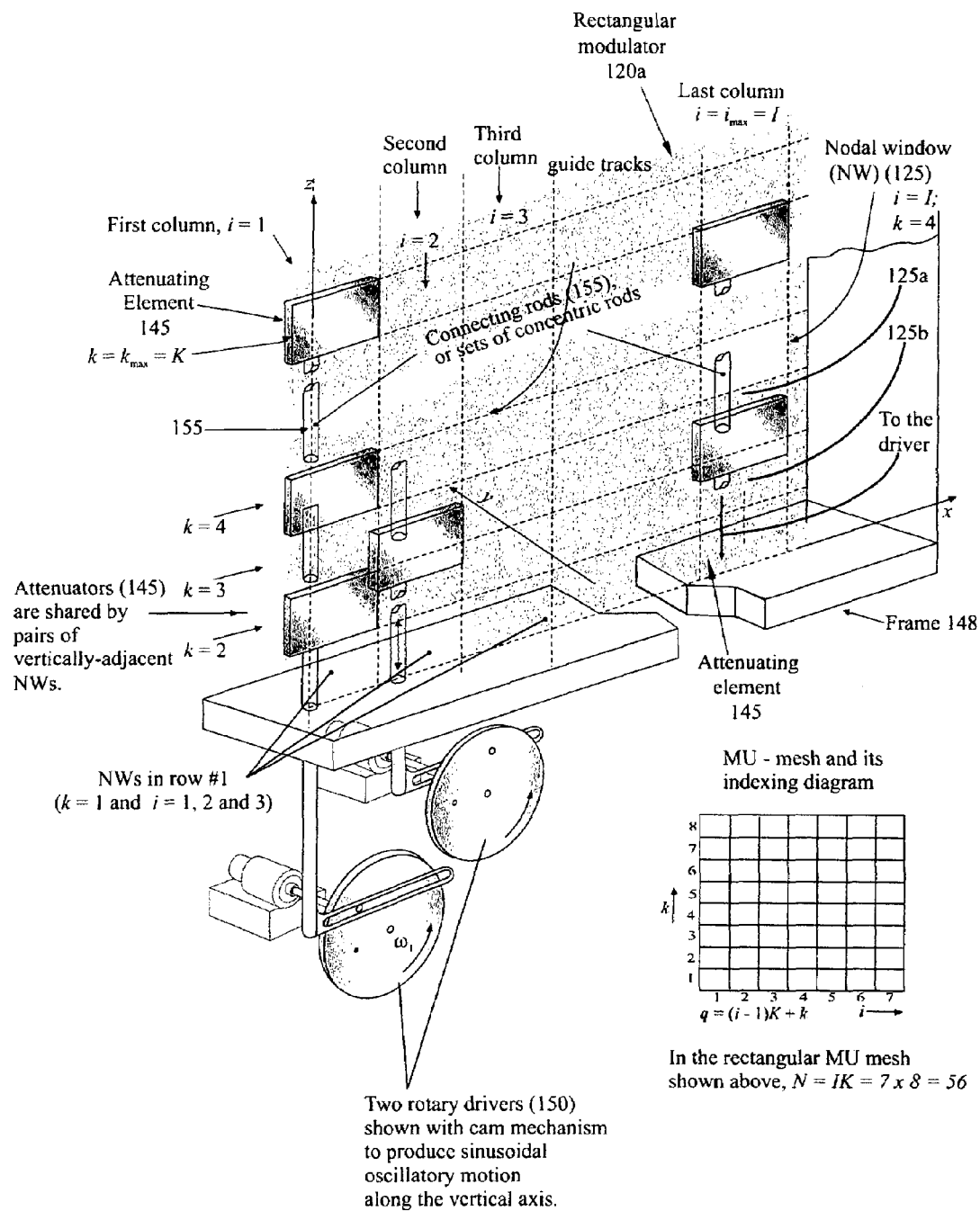
FIG. 4 depicts a rectangular modulating unit (Modulating unit) according to an embodiment of the invention.

In a simplified version of the rectangular modulating unit 120 shown in FIG. 4, each attenuating element 145, located in a column, may be attached to a common thin vertical rod 155, with spacing between adjacent elements in the column equal to or close to the vertical dimension of the window 125. A frontal view of the exemplary modulating unit column in FIG. 4 shows a series of connected elements alternated by vacant spaces, which make up a total of K passages in each column through which gamma rays may stream. The number K of passages may or may not be the same as the number N of nodal windows 125 in a column. This embodiment incorporates the sharing of one common attenuating element 145 by a pair (125a and 125b) of adjacent nodal windows in each column of the modulating unit, as shown in FIG. 4 when the attenuator 145 slides in an upward and downward motion.

The time-variant oscillation that modulating unit 120 imposes on the intensity of the gamma fluxes which pass through the modulating unit, is not uniform across the area of the modulating unit. Modulating unit 120 may be configured, in an embodiment, so that the time-variant oscillation varies in a two-dimensional space, across the plane (the cross-sectional area) of the modulating unit. FIG. 4 illustrates a view of the cross-sectional area of modulating unit 120 which may be designed to represent a matrix of window-like openings, referred to as "nodal windows" (NWs) 125 and their associated attenuating elements 145. Each attenuating element or attenuator 145 exhibits a unique time-dependent oscillatory gamma attenuation upon the portion of the gamma ray stream moving through the particular nodal window 125 towards detector 115 (or alternately, toward the inspected object 105).

The exemplary modulator unit 120 shown in FIG. 4 is designed for periodic translatory oscillation (e.g., sinusoidal) of the gamma attenuating elements. In the coordinate system selected, x is the lateral direction across the face of the modulating unit, y is perpendicular to the plane of the modulating unit (in the mean direction of the gamma flux), and z is the vertical direction in the modulating unit plane. Attenuating elements 145 may be rectangular slabs of tungsten mounted on vertical rods that move in the vertical direction. The array of such attenuators is made up if K rows and I columns in the (x, z) plane. Each elementary areal space in the (x, z) plane is designated as a nodal window (NW) 125 and is identified by the subscripts i (along the x direction) and k (along the z direction) representing the row and column, respectfully, in which the NW resides. The term nodal window may be represented by the symbol NW in the Figures. In each column, there may be an open space between adjacent attenuators, so that as the rods supporting the attenuators in each column oscillate up and down, each NW is alternately blocked and unblocked. Each depicted attenuator serves two vertically adjacent NWs in a column, causing the opening of one window to correspond to the closing of the adjacent window. All attenuators in the same column are connected to a common rod. A solenoid-driven sliding actuator may be used to substitute for the cam mechanism shown in FIG. 4. While electric power is convenient for the rotary drive, other power sources may also be used. The attenuators in each column can move along guide tracks, indicated by the vertical dashed lines. Alternately, upper and lower shaft bearings may be designed to serve as guides for shafts.

Figure 5:
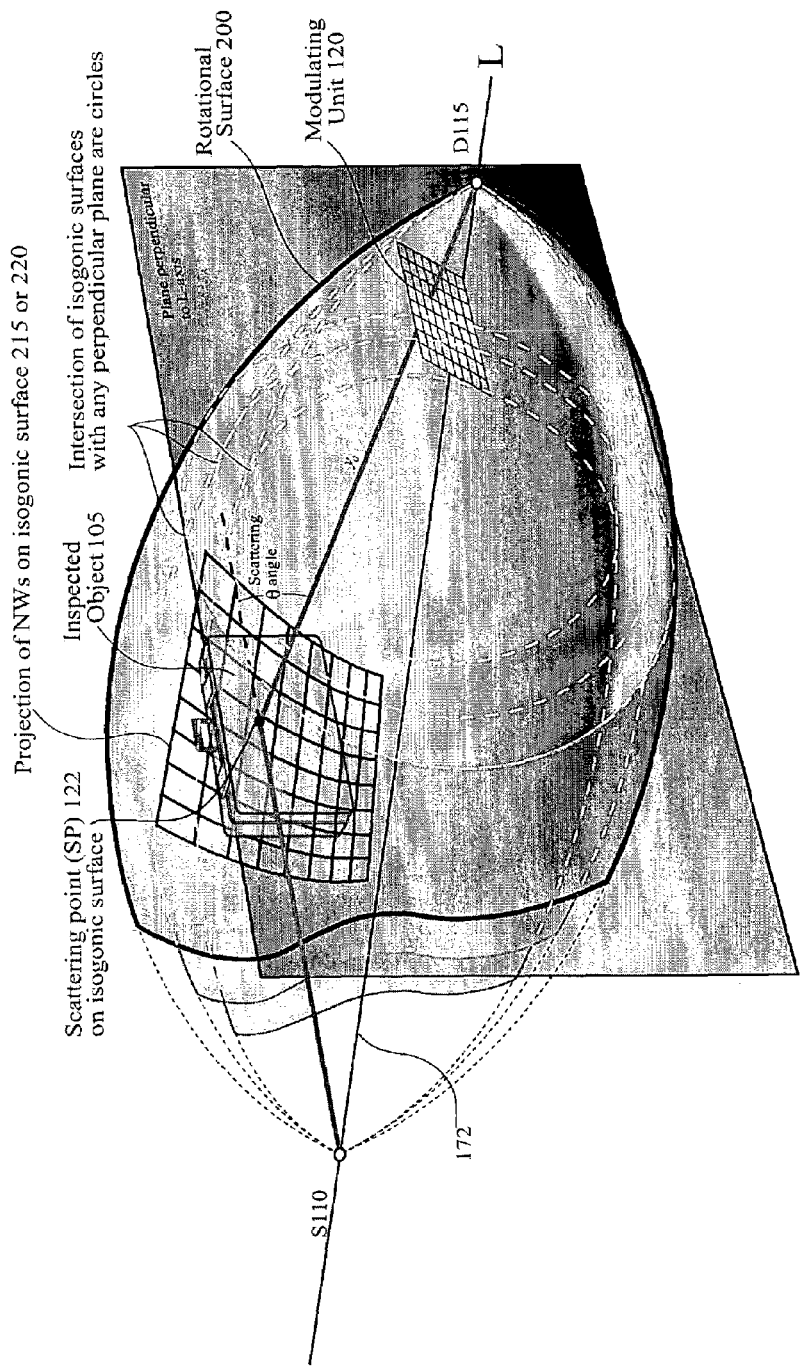
FIG. 5 is an illustration of the virtual projection of the modulation unit's nodal windows upon spheroidal isogonic surfaces according to an embodiment of the invention.

The modulating unit 120 may be placed in the path of the gamma rays so that the cross-sectional area is perpendicular to the average direction $y_o$ of the fluxes transmitted from inspected object 105 and arriving at the detector 115 (or alternately, from the source and arriving at the inspected object). The design and arrangement of the nodal windows 125 and their attenuating elements 145 enables the imposition of a unique time-dependent oscillatory attenuation of the particular gamma flux segment that passes through each window. By employing multiple windows, with each attenuating element moving independently of other elements, modulating unit 120 uniquely encodes each segment (defined by the nodal window) of the gamma stream cross section incident on the modulating unit (or alternately, coming from the source 110 and incident on the inspected object 105). Each of the solid-angle segments of the gamma stream is associated with its particular NW 125, and defines a solid angle through which the particular gamma flux propagates. The solid angle is the angle that the nodal window subtends with the detector 115 (or alternately, the source 110 when the modulating unit is positioned between the source and the inspected object) as the apex of the subtended angle. As a result, for the detected gamma rays which are scattered from any volumetric element (voxel) within the inspected object 105, the voxel's center being the scattering point (SP) 122 as shown in FIG. 5, and the resulting local flux intensity can be characterized and identified by association of the nodal window's location with respect to the corresponding voxel within the inspected object 105. The term voxel, which is derived from volumetric pixel, pertains to elementary, small, but measurable finite-difference volumes. The term local flux refers to the gamma flux emanating from the point of scattering SP within the inspected object 105. More precisely, the term local flux refers to the averaged flux from within its associated voxel.

Each attenuating element or attenuator 145 exhibits a unique time-dependent oscillatory gamma attenuation; the functional time variance generated within each nodal window 125 of the modulating unit represents the encoding of passing gamma fluxes and is window-specific. The functional time variance may be accomplished by means of translatory or rotary movement of the attenuating element 145 relative to the individual nodal window's frame 147. The frame of the nodal windows can be either a hardware component, or a virtual frame that defines the nodal window's boundary, resulting in virtual nodal windows. The movement of the attenuating element causes a partial blocking of the nodal window, as shown in FIG. 4, and affects the magnitude of each solid-angle segment of the gamma ray stream as the gamma rays pass through the modulating unit 120. This translatory movement may be generated, for example, by attaching rotary drivers 150, as shown in FIG. 4, to the base frame 148 of the modulating unit 120 to vary the position of the attenuating elements 145. The rotary drivers 150 of the modulating unit 120 enables movement of attenuating elements 145, through the use of any known connection devices such as a hinge connection, linking device, or rotating shaft.

In the embodiment shown in FIG. 4, of the total number of columns I; only the first and second of these columns including their rotary drivers are shown attached to their cam mechanisms, which can be driven by an electric motor. The rotary drivers may be designed to produce a sinusoidal oscillatory motion along the vertical axis of the modulating unit 120. The rotational motion of the rotary drivers 150 is transferred to the oscillating attenuating elements 145 to vary the time function of their attenuation. Thus, this movement of the attenuating elements 145 affects the flux of passing radiation within each solid-angle segment leaving the modulating unit 120, traveling on its way to the detector 115. A computer, capable of executing data processing instructions, can be coupled with or integrated within system 100 to control and execute the analytical functions of the invention. Also, through the use of a computer or similar device (not shown) the motion of the attenuating elements 145 may be programmed to result in amplitude modulation (AM), phase modulation (PM), frequency modulation (FM), or a combination thereof.

The design of the modulating unit 120 can be configured or modified so that the invention can be utilized in a variety of modulating unit configurations. However, as discussed above, the physical attributes of the inspected object may be a factor for consideration in designing the modulating unit for a particular application. The system 100 can be designed (among other options) to include a rectangular modulator 120a (FIGS. 4 and 6) or a polar modulator 120b (FIGS. 7 and 8). In the rectangular embodiment, modulating unit 120 may be configured as a two-dimensional rectangular array of gamma attenuating elements. The attenuators 145 may be fabricated in a number of different ways, for example, as discrete elements, virtual portions of a number (I) of helical (twisted) strips, or as a single monolith sine-curve shaped attenuating block (not shown), that slides laterally across the nodal window's cross-sectional area. The rectangular modulating unit in FIG. 6 may be designed for rotary movement, causing periodic flux variation in rectangular gamma attenuating elements 145 which may utilize the same coordinate system as for the modulating unit shown as in FIG. 4, retainiing the same notations for rows and indexing in the array of attenuators 145. Attenuating elements 145 may be rectangular slabs of tungsten mounted on vertical rotating rods. The illustration shows a modulating unit with 10 columns and 10 rows, corresponding to $N=IK=10\times10=100$ NWs. Representative sets of attenuators 145 are shown only in columns #1 and #2. Attenuator elements are shown in various orientations on the driving shaft. The attenuation that each element offers is maximum when the face of the element is aligned with the face of the modulator unit frame (perpendicular to the direction of incoming gammas), e.g., in the NW corresponding to $i=1$, $k=10$ in the illustration. The attenuation is least when the attenuator element is perpendicular to the face of the Modulating unit (e.g., in the NW corresponding to $i=1$, $k=6$ in the illustration). The attenuation in each column can be made unique by the imposition of a different velocity of rotation of the supporting shafts. Uniqueness within the same column is achieved by the variation of the angular orientation of elements on each shaft (resulting in a phase lag). The thickness or height of particular attenuators can also be varied. The attenuation in a representative NW is characterized by the modulating function a(q, t). In it, $P_q$ is the phase lag of NW #q. The driving mechanism for each column shown employs electric motors, but other power sources may also be used.

Practical values for oscillatory modulation frequencies, selected by a user, may be within an order of magnitude of one per second. A suggested size for the modulating unit 120a may be between approximately several inches and a few feet in the lateral direction (perpendicular to the $y_0$ axis, representing the average direction of the gamma-propagation trajectories), with the thickness (in the direction of gamma-propagation) of the modulating unit's attenuator elements of the order of a fraction of an inch. The attenuator thicknesses may be influenced by the kind of gamma attenuating material selected. The modulator unit dimensions may be influenced by the scale of the overall size of the inspection system, especially considering the dimensions of the inspected object and the distance from the source and the detector.

In the simplified illustration of the rectangular modulating unit 120a shown in FIGS. 5 and 6, tungsten attenuating elements 145 are arranged in a matrix of I columns and K rows, forming a two-dimensional rectangular array of nodal windows 125, with the surface area of the window-array oriented perpendicular to the average direction $y_0$ of the oncoming gamma rays. The dimensions of the nodal windows may be the same or may vary throughout the entire modulating unit. Likewise, the thickness of the attenuating elements may be uniform, or vary from window to window.

Observing the dynamics of the system 100, when vertical driving rod 155 is in the lowest position, each nodal window 125 in the column is either clear or covered by an attenuating element. The invention may be designed so that when the rod is in the lowest position, all odd-numbered nodal windows may be blocked (providing maximum attenuation of their incident gammas), and all even-numbered nodal windows are clear (providing no attenuation of their incident gammas). When drive shaft 155 is at the highest position of its translatory oscillation, the situation is reversed so that all odd-numbered nodal windows are clear, while all even-numbered nodal windows are blocked and provide maximum attenuation to the incident gammas. As drive shaft 155 moves between the lowest and highest positions, all nodal windows undergo some degree of attentuation between the minimum and maximum attainable with their respective attenuating elements. The blocked and clear states of window transmission may vary in a sinusoidal (or other trignometric function) manner as a consequence of the changing positions of attenuating elements, which is time-variant, as controlled by the sinusoidal (or other trignometric function) oscillation of the vertical drive shaft 155.

In each column of modulating unit 120a shown in the example configuration of FIG. 4, a single vertical drive rod 155 supports several similar-sized gamma-attenuating slab-shaped attenuating elements 145. If each attenuating element slab 145 is shared by two adjacent nodal windows, the number of nodal windows for each column is N=2×5=10 NWs (for five such elements in a column). Each of the attenuating elements 145 may be designed with its unique thickness and height. All the attenuating elements 145 in a column may move at the same frequency since they are driven by the same drive shaft. However, the invention may also be configured so as to include separate (for example, concentric) drive shafts to control each attenuating element 145 individually so that the oscillation frequency of the elements may differ from each other. Also, each such individually-controlled attenuating elements 145, when moving independently of the others, could do so with its own time delay (phase lag) in motion.

Similar to the distinctions caused by varying the size (and/or even the material) of individual attenuating elements 145 within the columns of the rectangular modulating unit, operational distinctions in phase and frequency may also be incorporated to further generate unique variations of the gamma flux attenuation in each nodal window. The attenuating elements 145 can be oscillated up and down, individually or as a group, or by varying in time the position of individual attenuating elements within its associated nodal window. As depicted in FIG. 4, additional columns of attenuating elements are placed adjacent to the first column, making a total of I columns within the modulating unit. Each of these columns can be operated at a different oscillation frequency. For example, if I=40 such columns are included in the system, then the total number of uniquely oscillating absorbing elements would be 40×5=200. This embodiment provides twice that number (400) of uniquely-modulated nodal windows, since one attenuating element 145 serves two adjacent nodal windows 125, as discussed above and shown in FIGS. 4 and 6. Thus, the areal cross-section within the volume of the inspected object would include 400 pixels, corresponding to 400 voxels for each isogonic slice.

Of course, one having ordinary skill in the art will readily understand that the number of pixels (and the corresponding spatial resolution), may be designed to any convenient configuration, and the parameters of the modulating unit may also be of variable design. For instance, FIG. 6, which depicts an option for the operating rectangular modulating unit 120a, includes the vertical shaft 156 that turns the individual twisted rotating attenuating elements, instead of the vertically-moving elements as shown in FIG. 4.

FIGS. 7 and 8 illustrate an alternative embodiment depicting a polar modulating unit 120b. The polar modulating unit 120b may be designed using the same general concept as that of the rectangular modulating unit 120a, with a few notable exceptions. The polar modulating unit 120b includes a circular disk 152 fabricated of gamma attenuating material such as tungsten or lead. The disk 152 may be divided into a set of I concentric bands 153, all of which can have the same value of radial width $\Delta r^*$. Either the radial width or the thickness of the tungsten attenuator in each of the concentric bands 153 may be varied in order to generate a sinusoidal attenuation of the gamma flux. In other words, the amount of attenuation experienced by the portion of the gamma flux passing through a nodal window 125 of the disk 152 may be dependent on the designed variable radial width or the variable thickness (governing the attenuating power) of the attenuating material at the location of the nodal window 125. That nodal window 125 is a virtual entity, contained in a fixed position on the virtual stationary array of nodal windows superimposed on the rotating disk 125 of the modulating unit 120b. The nodal window area may be defined by the expression $[r^* \cdot \Delta\beta^* \cdot \Delta r^*]$. As indicated in FIG. 8, the symbol $\Delta\beta^*$ denotes the sector angle (of the order of degrees), the symbol $r^*$ denotes the radius, and the symbol $\Delta r^*$ denotes the width of the radial band. Reiterating the explanation provided with regard to the embodiment of the rectangular modulating unit 120a, variation in the attenuating power at a nodal window 125 may be the result of either a variation in thickness of material in the direction of propagation of gamma rays as they travel toward the detector/spectrometer 115, or a variation in radial width of the material inside the concentric bands 153.

In the polar modulating unit 120b, frequency modulation (FM) and phase modulation (PM) executed simultaneously provide a preferred method of effectively encoding each individual solid angle segment of the gamma flux passing through the modulating disk and arriving at the detector. This encoding is specific to particular locations on the virtual stationary circle, on which a nodal window 125 is defined by the radial band of width $\Delta r^*$, radius $r^*$, and polar angle $\beta$. These geometric pointers are associated with representative scattering points, i.e., the centers of scattering voxels, with their finite-difference area defined as conical projections of the virtual shadow of the nodal windows on the isogonoic slices within the inspected object, as viewed from the detector.

FIG. 7, specifically, depicts how the time-varying attenuation may be generated in the invention when the thickness of the material is varied in the direction of propagation of the gamma rays in the polar modulating unit 120b. FIG. 8 illustrates an example of how the invention's modulating unit may be designed by varying the radial width of the attenuating material. The detector 115 views the inspected object by sensing scattered gamma rays impinging on the detector. For each pair of values $(r^*, \beta)$ the corresponding gamma-attenuating material performs a periodic attenuation according to the size and shape of the attentuating material and its motion. The radial band #i has i peaks of the sine curve, the next radial band has (i+1) peaks, etc. The number of peaks defines the modulation frequency for the band under consideration for any given speed of rotation of the disk. In general, the polar modulator shown in both FIGS. 7 and 8, can be designed to rotate with a constant, relatively slow angular velocity (of the order of 1 to 10 revolutions per second) about its center.

As an example, five concentric bands (with average radii $r_4^*$, $r_5^*$, $r_6^*$, $r_7^*$, and $r_8^*$) are shown in the polar modulator 120b in FIG. 7. There is a graduation of shading, from very light to very dark, going along the circumference. In this embodiment, the dark regions represent the positive peak areas of a sine-wave variation in thickness of the attenuator material—or maximum thickness—and the light areas represent negative peak areas, or minimum thickness. The attenuation of gamma rays passing through the disk is greatest at the location of the dark areas (where the material is thickest), and least at the light areas (where the material is thinnest). The band centered at a radius $r_7^*$ has seven very dark areas, representing seven complete sine-wave cycles. Each positive peak in that band is separated around the circle by an angular interval $\Delta\beta$=51.4 degrees. The next outer band, $r_8^*$, has eight cycles, separated by an angular interval $\Delta\beta$=45 degrees. As the disk 152 turns through one complete rotation of 360 degrees, each band may be out of phase with the next outer band by one complete sine-wave cycle. The sine-wave frequency is a bit higher for each successive outer band. For example, the band at $r_8^*$ experiences eight cycles in the same time period (one rotation of the disk) that it takes the next inner ring to experience seven cycles. The next two inner bands exhibit six and five cycles, respectively, with increasingly lower frequencies. This illustration can be expanded to incorporate any number of concentric bands. Further, the positions of bands having specific frequencies of oscillation, may be ordered in any sequence.

During a steady rotation of the disk 152, the traversed arc-length measured with respect to a stationary point next to the disk is proportional to time. Therefore, phase modulation PM is a characteristic that naturally occurs in this embodiment. For such a situation, the following may be implied: consider two adjacent nodal windows 125 in the same radial band of the polar modulating unit as shown in FIG. 7. If the attenuation in the left nodal window corresponds to a peak of the sine wave, then the right nodal window experiences a smaller, slightly delayed, off-peak attenuation. With clockwise rotation of the modulating unit 120b, the sine-wave peak moves to the right nodal window, leaving the left nodal window with a smaller off-peak attenuation. The difference in the attenuation between these two nodal windows is characterized by a time lag which is proportional to the phase angle difference $\Delta\beta$ between the left and the right nodal windows on the radial band. Related to the use of phase modulation, the sizes (thus, the boundaries) of the nodal windows in the polar modulating unit are also completely adjustable. Analogous to the options described with respect to the rectangular modulating unit employing rotating elements with helical attenuators 120a, the user of the polar modulator may also select values of the phase angle increment $\Delta\beta$ merely by entering a numerical parameter into the data processing computer program, without any adjustment of the physical apparatus.

For example, if the measurement system is set to resolve a difference in gamma intensities corresponding to $\Delta\beta$ equal to a 10 degree phase shift, then the polar modulator system would have K=360/10=36 phase delays (corresponding to 36 nodal windows along a column of a rectangular modulating unit 120a). The user can select the design of a system with I selected concentric bands. If I=20 is selected, there would be K=I=36×20=720 pixels of information per virtual slice of the inspected object, which pixels are available to reconstruct the image of one isogonoic slice within the inspected object. Use of finer phase resolution (e.g., by choosing $\Delta\beta$ less than 10 degrees) together with additional radial bands in the modulator disk 152 can provide for several thousand pixels in a reconstructed image of an isogonic slice. Using 720 pixels per slice, if 20 slices are considered (i.e., 20 energy values of scattered gammas), the resulting resolution would be represented by 720×20=14,400 voxels inside inspected object 105.

While in FIG. 7, the thickness of the attenuator in the direction of gamma-propagation directly controls the nodal window-associated attenuation, that attenuation is controlled in FIG. 8 by varying the radial width of the band so that the gamma-attenuating area of the band at any point along its circumference varies in a sinusoidal manner, as depicted by the shaded area specifying the attenuator material exposed to gamma rays in a band's sector.

The design in FIG. 8, being is analogous to the design of FIG. 7 in regard to the periodic sine variation of attenuation, enables: (a) amplitude modulation (AM) as a result of the changing thickness of the attenuator material along the circumference of the disk; (b) frequency modulation (FM), utilizing the radial variation of the number of sine wave cycles; and (c) phase modulation (PM), having intrinsic phase delays among adjacent virtual nodal windows on each particular radial band, with a wide range of practical options for selection of the phase angle $\Delta\beta$ (i.e., time delay) between adjacent nodal windows.

In both polar modulating unit designs, the use of band-related FM supports the determination of the sub-total of gamma fluxes—i.e., all fluxes passing through any particular annular band—which is a component of the total flux passing through the entire cross-section of the modulating unit disk, i.e., through all its annular bands.

Regardless of the configuration, the modulating unit 120 constitutes a two-dimensional matrix of periodic, time-varying gamma attenuators, which modulate the gamma fluxes passing through the attenuator-associated nodal window.

Further, in an alternate embodiment of the invention, the modulating unit maybe configured in a three-dimensional geometry, wherin the modulated gammas pass through more than one layer of nodal windows and their associated attenuators to serially-encode the individual streams of radiation.

The Integrated Modulator

As an alternative embodiment, instead of utilizing a separate modulator unit as described in the preceding discussions, the invention may be configured so that a modulator is incorporated as an integral part of either the detector or the radioactive source.

To integrate the modulation unit within the detector system 115, the system 100 may be configured by adapting the detector/spectrometer into a mosaic, with individual read-out from each element of the mosaic [is possible]. Such a configuration would allow the signals, generated by the incoming gamma rays incident on each mosaic detector element to be segregated and processed separately. Electronically controlled modulation of the bias voltage (in the case of a semiconductor detector) or a varying mosaic light filter (in the case of a scintillator and photo-multiplier tube detector) may impose the modulating function a(q, t), as described below, on the incoming signals. This signal perturbation would be equivalent to the operation of the external modulating units described earlier.

Alternatively, the modulation unit may be integrated with the radioactive source system according to the following manner. A customized stationary attenuating slab may be precisely shaped to produce a varying attenuation (along its length) of gammas traveling in a direction approximately perpendicular to the surface of the slab. As the source is raised from its storage position to irradiate the inspected object 105, the source would travel past the shaped attenuating slab. Thus, the source's two-stroke motion in and out of the shield cask would result in a designed modulation of the passing gamma flux according to the slab design, generating a transient (time-dependent) attenuation of the source gammas. This will result in a modulation of these gamma rays analogous to the a(q, t) modulation function impressed by the attenuator elements in the modulating unit.

Radiation Detector Requirements

Referring back to FIG. 1, the radiation detector 115 may be a gamma spectrometer, which is a device that detects individual gamma photons that impinge upon the detector 115 and provides an output signal that is proportional to the energy of the detected gamma photons. The size of the detector may be configured to be small in comparison to the size of the inspected object 105 and to the distance between the detector 115 and the inspected object 105. In the analysis performed by the invention, the detector may be approximated as a point in space, to simplify the geometrical assumptions in the analysis.

During operation of the system 100, optimal positioning of the source and detector is partially dependent on the size and shape of the inspected object 105, with the cone of radiation emerging from the source directed toward the inspected object 105, encompassing the region to be inspected.

Compton Scattering of Gamma Rays

The operation of the inspection system 100 also takes advantage of the relationship between the energy of scattered gamma rays and the angle of scattering, expressed as the Compton Law, and explained by H. Semat, *Introduction to Atomic Physics*, Rinehart & Company, Inc. Publishers, New York, 1947, pp. 144-145 and J. R. Lamarsh, *Introduction to Nuclear Engineering*, 2d ed., Addison-Wesley Publishing Company, 1982, pp. 81-88. Both of these publications are hereby incorporated by reference.

As shown in FIG. 2, the Compton Effect refers to the process in which a gamma photon or X-ray of energy $E_o$, incident on a target, interacts with the atomic electrons in the target material. This process results in a scattered photon being emitted at an angle $\theta$ from the direction of the incident photon with a reduced energy E', and a recoil electron emitted at an angle $\theta^*$.

The relationship between the energy of the scattered photon and its angle of emission has been established and reviewed by a number of authors. Lamarsh notes that the energy-angle relationship for Compton scattering is given by the expression in Equation (1) below.

$$E' = E_o E_e / [E_o(1-\cos\theta) + E_e] \qquad \text{Eq. (1)}$$

E' is the energy of the scattered photon, $E_o$ is the energy of the incident photon, $\theta$ is the angle of deviation of the scattered photon from the direction of the incident photon, and $E_e = m_e c^2 = 0.511$ MeV is the rest-mass energy of the recoil electron.

For a mono-energetic incident gamma flux and defined source location, the Compton relationship allows one to determine the angle (i.e., the direction) from which the scattered gammas originated, based on the measurement of the energy of detected scattered gammas. A gamma ray detector/spectrometer 115, such as described above, may be used to separate out the energies of the gamma counts registered by the detector 115. Employing such instruments over a broad range of energies enables system 100 to simultaneously measure the energies and the intensities (count rates) of all detected gamma photons, which are predominantly scattered within the inspected object 105. This measured energy spectrum of scattered gamma photons and their associated count rates (proportional to the magnitude of the flux of scattered gammas) are geometrically related to the corresponding directions and locations in the examined space.

Formation of Isogonic Surfaces

A triangle, as shown in FIGS. 3A-C, may be formed by three points in a plane including the location of the radiation source at point S; the location of the scattering point at point SP somewhere within the inspected object; and the location of the detector at point D. The distance between the point S and the point D is L* (the base of the triangle), shown as segment 172.

The Compton energy-angle relationship can be illustrated by the geometrical attributes of such a triangle. For example, if a half-circle is drawn above a triangle's base, with the circle's center in the mid-point of the base, wherever the upper tip of the triangle is located on that arc, the subtended angle from that tip (towards the triangle's base) will always be 90 degrees (as shown by Case II of FIG. 3b). This axiom can be extended to the more general case: if the system deals with a smaller (flatter) arc of the circle rather than a half-circle—meaning that the center of a new circle would be below the middle of the base of the triangle—all the new subtended angles will again be equal among themselves, but smaller than 90 degrees (Case I of FIG. 3a). Each tip-angle is a function of the length of the new arc's radius; that depends on how far the center of the new arc is below the mid-point of the triangle's base. Conversely, if the center of a new arc is above the triangle's base, such an arc would not be flatter, but more curved (Case III of FIG. 3c). The arc's center location and its radius are known functions of the distance L* and the scattering angle $\theta$, as derived and initially published by N. Kondic, *Density Field Determination by an External Stationary Radiation Source Using a Kernel Technique*, Symposium on Poly-phase Flow Measurement, ASME Winter Annual Meeting, San Francisco, Calif., December 1978. The subject matter of this publication is also hereby incorporated by reference.

The above observations may be applied to two-dimensional space. However, it is within the scope of the invention to extend and apply these observations to three-dimensional space. Any of the arcs considered here can be rotated about the triangle's base, which is denoted as the line that joins the source and detector points referred to as the S-D segment 172 in FIG. 3. Such a rotation creates a surface, which, in the case of relatively flat arcs, may resemble a blimp 200, as shown in FIGS. 3*a* and 5. In this manner, the constant scattering angle is actually associated with all points on the arc-generated surface of rotation, where each such surface's shape corresponds to a particular value of the scattering angle θ. These surfaces are referred to as isogonic surfaces, since each surface of rotation is the locus of scattering points for gamma photons emanating at the same scattering angle. The portion of the isogonic surface within the inspected object is referred to as the isogonic slice (FIGS. 5 and 9); it forms the loci of scattering points producing gamma fluxes within the cone of view of the detector (the $y_o$ axis is in the mean direction of the inspected object's depth measurement). When the scattering angle θ changes, the shape of the rotating isogonic surface will change (it will become more flat or more curved), and according to Eq. 1, the energy of the scattered gamma rays will also change. FIGS. 3A-3C illustrate the dependence of the isogonic surface's shape on the scattering angle θ. From a flat blimp shape 200, corresponding to smaller scattering angles, that shape becomes a sphere when θ reaches 90 degrees. When the scattering angle increases beyond 90 degrees, the contour swells into a double spheroidal shape. FIGS. 3A-C illustrate the geometric aspect of Compton's Law that lends itself for application by a device which may be employed in the invention. In summary, Compton's Law may be applied to the invention by utilizing any of the three types of isogonic surfaces: Case I—Oblong rotary surface with pointed poles (the SD segment is located above the circle's center) (FIG. 3*a*); Case II—Sphere (the SD segment passes through the center of the circle) (FIG. 3*b*); and Case III—double spheroidal rotary surface with indented poles (the SD segment is below the circle's center) (FIG. 3C).

The application of Compton's Law to the inspection measurements performed by the invention allows the system 100 to yield information on the distance along the path of gamma rays emanating from the source, with scattering points forming a defined curved isogonic surface (FIG. 5) of a known shape that intersects with the distance axis $y_0$ along the gammas' trajectory. The novel modulators (described above) are used in a determination of the distribution of single-scattered gamma fluxes across the isogonic surface, i.e., along the two remaining axes of the inspected three-dimensional density field, these being x and z for rectangular modulators, and r* and z for polar modulators.

The modulating unit 120 may consist of a two-dimensional matrix of time-varying gamma attenuators 145, which modulate the fluxes passing through them. The modulating unit 120 is placed in the path of the gamma rays, either between the source and the inspected object or alternately, between the inspected object and the detector. Considering the latter position, each particular segment of "local" scattered gamma flux of constant intensity (associated with a particular voxel) incident upon a particular nodal window of the modulating unit can be encoded in time, by varying its intensity in time while passing through a nodal window. The modulation, i.e., the encoding imposed on flux segments, is unique for all flux segments coming out of any particular voxel (volumetric pixel) located along a given axis $y_q$ within the inspected object. Such flux segments pass through the $q^{th}$ nodal window which is associated with a particular axis $y_q$. The modulation may be decoded from the signal output of the detector 115, employing a multi-stage data-processing system to yield the flux of scattered gamma rays as a function of three coordinates of the scattering point (or voxel): two directions ($x_q$ and $z_q$) across the modulating unit 120, the third being the depth $y_q$ within the inspected object 105. The third coordinate may be obtained from the known location of isogonic surfaces, derived from the gamma energy-angle relationship cited in describing the Compton scattering process, as discussed above.

In accord with the cited Compton Law, for a particular source energy $E_0$, anywhere in the surrounding space where the scattering angle is constant, the Compton scattering phenomenon: (a) results in the same measurable energy of scattered gamma rays, and (b) has to occur on a particular isogonic surface, noting that the location and shape of such surfaces are independent of the presence, shape, material, and size of any inspected object and its internals.

Therefore, from these geometrical attributes, the invention demonstrates that, when a mono-energetic radiation source emitting gamma rays into the surrounding space is placed at one fixed end-point of the isogonic arc and the detector is placed at the other fixed end-point of the same arc, an isogonic surface (that includes all the arcs forming it) can be completely defined for a given energy of the scattered gammas. That surface of rotation comprises all the loci within the surrounding space, which send constant-energy single-scattered gammas in the directions specified by the scattering angle θ, including the direction of the detector.

For any scattering angle and the corresponding shape of the associated isogonic surface, within small finite energy intervals in which finite numbers of scattering events occur, gamma photons can be detected. Each isogonic surface may be associated with a certain finite thickness, so that, in practical application, the invention deals with thin volumetric entities built upon the isogonic surfaces. These entities are termed isogonic shells. Since the source and detector are external to the inspected object, the widely extended isogonic shells virtually intersect with the inspected object. The portion of the isogonic shells that extend beyond the boundaries of the inspected object (as illustrated in FIG. 5) need not be considered. The useful portion of the isogonic shells, which are confined by the object's boundaries are termed isogonic slices. Since the isogonic slices are geometric notions rather than physical entities, they are referred to as virtual slices. The virtual slices are thin three-dimensional portions of the fully-extended three-dimensional virtual isogonic shells. The intersections of the inspected object and isogonic shells can result in various geometrical configurations of virtual slices, some of them illustrated in FIGS. 5 and 9.

Figure 9:
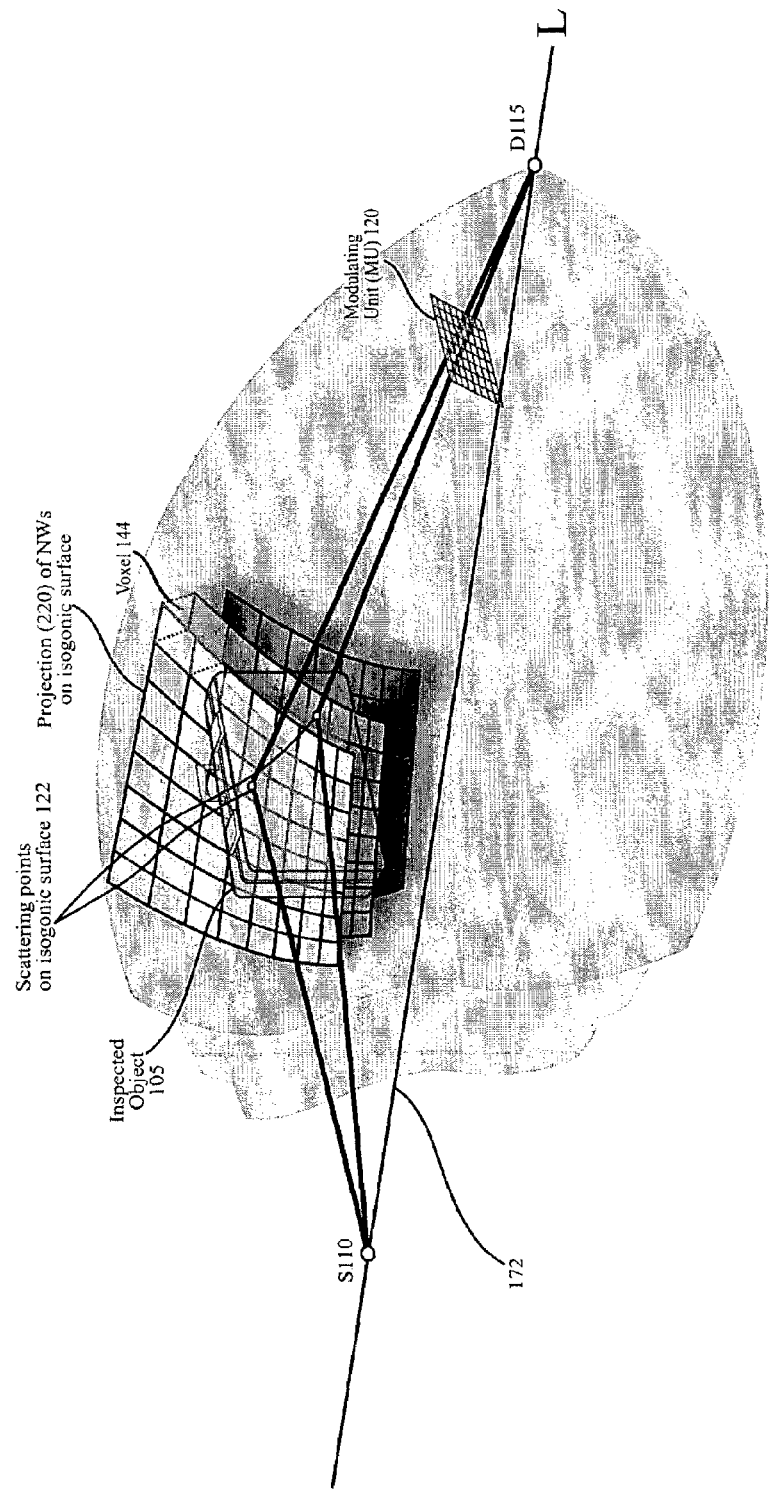
FIG. 9 shows a virtual projection (viewed from the detector), of a rectangular array of nodal windows on isogonic shells and surfaces within and around a proximate region of the inspected object, forming virtual voxels from which scattered gammas emanate and travel toward the detector.

The pyramidal projection 220 of the rectangular modulating unit's nodal windows (FIG. 9) may intersect all the isogonic surfaces and their associated thin shells, thus projecting curved quasi-rectangular patterns upon the slices within the inspected object 105. As can be seen in FIGS. 5 and 9, the contour of these patterns follows the shape of the curved isogonic slices introduced earlier. Since each such slice is a portion of its corresponding isogonic shell (which is the loci of all the scattering events resulting in gamma rays of the same energy emerging from that shell and registered at the detector), the total number of observed slices is the same as the number of isogonic surfaces and shells. That number, equal to $J=j_{max}$, is also equal to the number of energies ($E_1'$, $E_2'$, ... $E_j'$, ... $Ej'$) of single-scattered gamma rays considered in the analysis as well as of the number of energy bins utilized in the multi-channel pulse height analyzer.

FIGS. 5 and 9 depict an illustration of spatial scattering geometry upon spherodial isogonic surfaces with scattering angles ≦90 degrees. As indicated in FIG. 1 and stated earlier, the gamma rays that are emitted by the radioactive source, prior to scattering interactions within the inspected object, retain their original energy and direction (radiating isotropically from the point source). However, the scattered gamma rays, which are generated when the primary gammas interact with atoms, are predominately generated within the space inside the inspected object, which is filled with virtual isogonic slices, defined earlier to be of small, but finite thickness. An example of the orientation and size of the virtual slices is depicted in FIG. 9. This sub-division of the inspected object's volume into a finite number of virtual slices aids in the data acquisition and processing, and is related to the desired spatial resolution and optimal placement of the source, detector, and the inspected object.

Figure 10A:
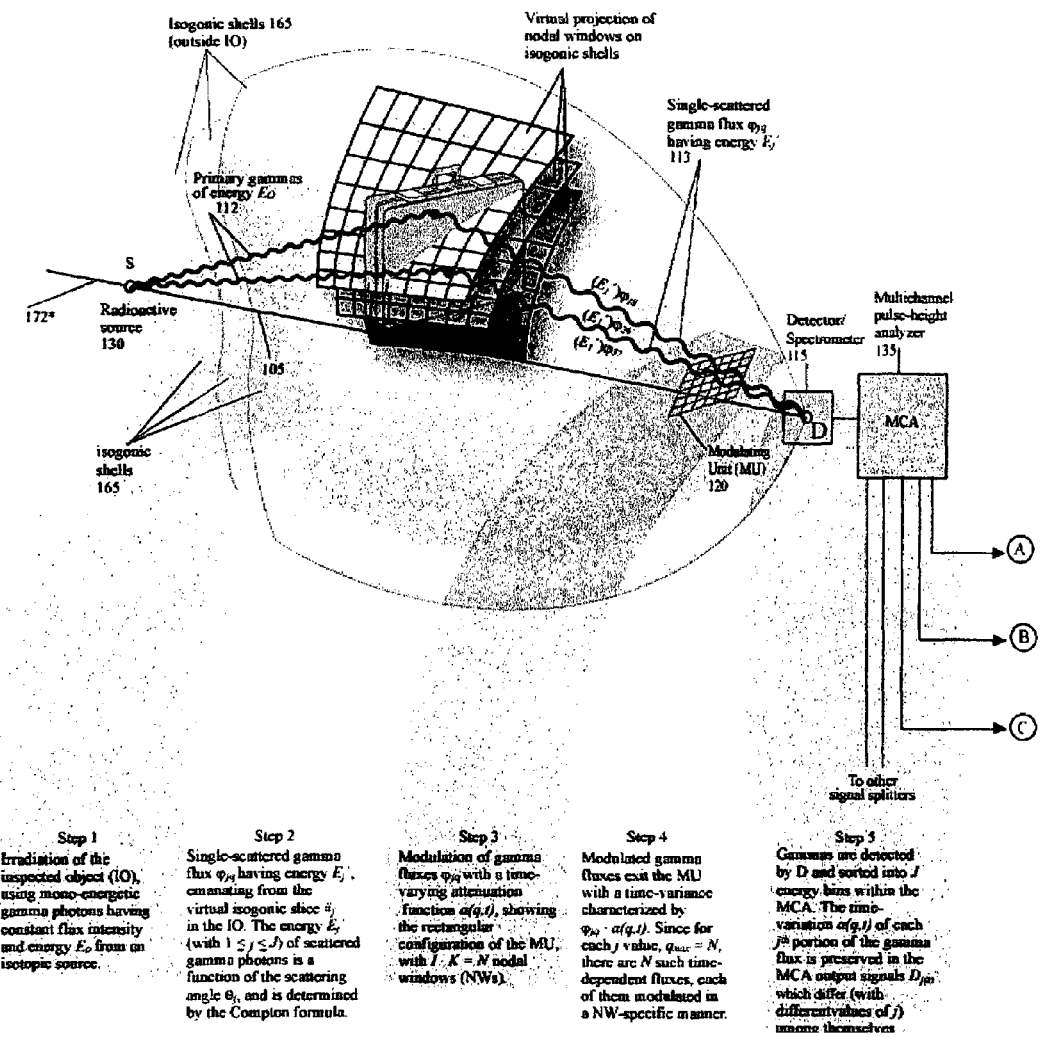
FIGS. 10A-10B illustrate operational flowcharts according to a method of the invention.

Referring to FIG. 9, the grid 215 (with N nodal windows corresponding to N voxels 144 per slice), represents the virtual projection upon the surface of isogonic shell #1, of all N nodal windows in the modulating unit 120. Gamma rays from the radioactive source scatter in any of the J isogonic shells; for simplicity, only shells 165a, 165b, and 165c (in the vicinity of the inspected object) are shown in FIG. 10A. A portion of the scattered gamma rays passes through the modulating unit as they travel toward the detector (D) 115, where gamma counts caused by detection of gamma rays arriving from particular isogonic shells are stored in separate bins of the MCA 135. The energy of the detected gamma rays (which are registered by the detector/spectrometer and MCA) provides a direct link to the isogonic slice (#1, #2, ... #i, ..., or #J) from which the gammas are scattered.

In summary, single-scattered gamma rays which reach the detector are generated within a selected number J of virtual shells. The portion of each virtual shell 165 that is within the inspected object is called a virtual slice, and represents a thin volumetric section of the inspected object. Each shell 165 is virtually illuminated by an expanded, pyramidal (for the case of the rectangular modulator—or conical, for the case of the polar modulator) projection 220 of the modulating unit. This virtual projection 220 occurs from the pyramid's (or cone's) apex at the detector, looking towards the inspected object. Since the $y_0$-axis passes through that apex (which is the center of the detector) and the center of the modulating unit's cross-sectional area, the $y_0$-axis also passes through the centers of the modulator's projection on all virtual slices, thus specifying their location, as indicated in FIG. 9. Since the energy $E_j'$ of each scattered gamma ray geometrically defines a specific j-th isogonic slice, the value of $y_{0j}$ (which is the inspected object depth coordinate) at the intersection of the y-axis and the j-th isogonic virtual slice becomes known, and can be denoted by $y_0(E_j') = y_{0j}$. Accordingly, based on a measurement of the energy of single-scattered gammas, the system can determine one of the spatial coordinates $y_{0j}$ of any j-th slice, on which the scattering points are located within the inspected object. Regarding the scattered gammas, the output signal of the gamma detector/spectrometer D is continually inputted into the MCA 135, which sorts the various scattered gamma counts according to their voltage pulse height (energy). Each of the J energy bins of the MCA 135 stores and displays the gamma counts during any given measurement period. These counts correspond to the detected scattered gamma photons having energy values within the bin's narrow energy band $\Delta E_j'$, with energy $E_j'$ in the center of the band. The number of counts stored in the $j^{th}$ bin represents sub-totals of the gamma fluxes and encompasses all scattered gamma photons from within a particular entire isogonic shell. Therefore, the counts consist of gamma fluxes from all individual voxels within the isogonic slice 165 (within the inspected object) and the portion of the isogonic shell 165 outside the object. All of these gammas have the same energy, $E_j'$. The total set of gamma fluxes scattered from the observed portion of the inspected object is the sum of sub-total modulated fluxes, encompassing all gammas scattered from all J isogonic slices (summed up from all J bins of the MCA 135), and which pass through the modulating unit 120. Another aspect of the invention is to identify and separate gamma fluxes which originate from scattering events occurring in a large number of volumetric elements included in an isogonic slice. These elements are individual voxels 144 having a known location and shape. The separation of fluxes enables the invention to calculate the magnitude of local fluxes coming from the individual voxels 144. At the same time, the invention is also capable of eliminating from consideration those single-scattered fluxes arriving at the detector from portions of isogonic shells 165 external to the inspected object. Those fluxes do not bear information on the density field inside the inspected object. Those fluxes do not bear information on the density field inside the inspected object.

Operational Diagram of the Inspection System

Figure 10B:
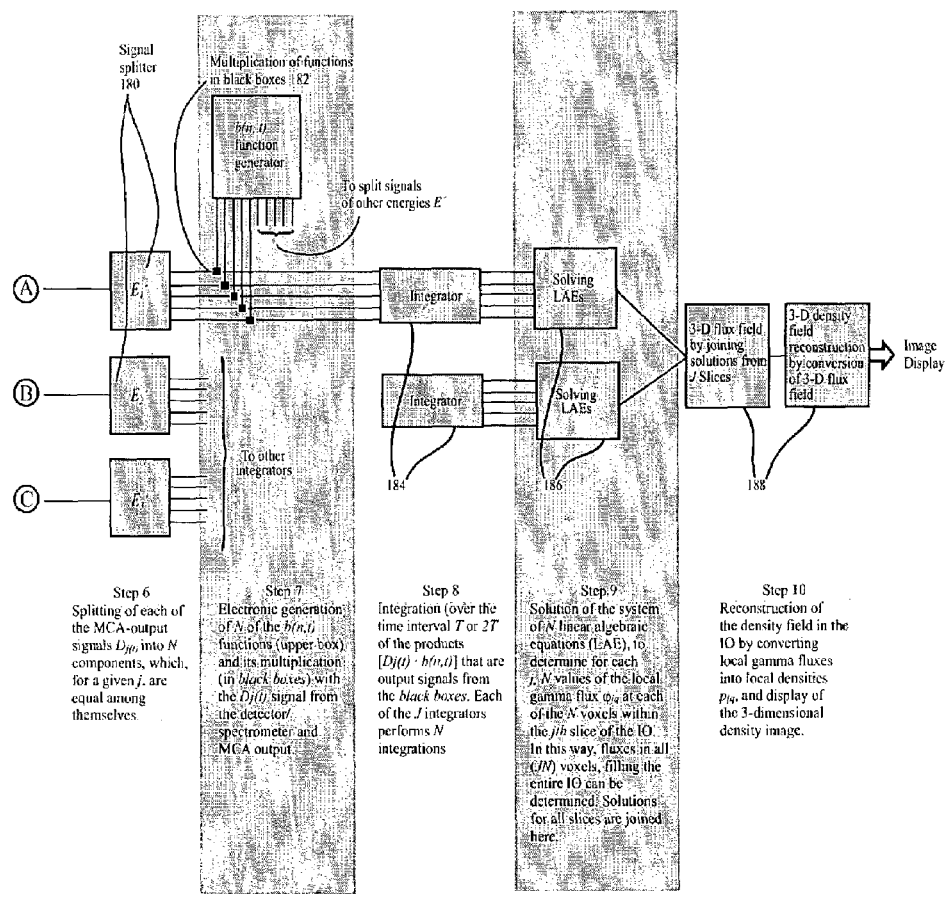

FIGS. 10A-10B provide a diagram of the process of generating three-dimensional images according to an embodiment of the invention. In Step 1, an inspected object is irradiated by gamma rays emanating from an isotopic source 130. The isotopic source 130 may be, for example, a mono-energetic gamma source having a constant stream of gammas with energy $E_o$. As shown in FIGS. 1-2, when the gamma rays interact with atoms inside the inspected object 105, scattered gammas 113 having energy E' are emitted from voxels within the inspected object and a measurable fraction of the scattered gammas 113 travel in the direction of the modulator 120 and the detector 115, in this particular embodiment.

In Step 2, the single-scattered gamma flux $\phi_{jq}$ having energy $E_j'$, which emanates from the virtual isogonic slice #j in the inspected object, passes through the $q^{th}$ nodal window of the modulating unit, and detected by the detector, is determined by the invention. By applying the Compton Law for an incident gamma energy $E_o$, the scattered gamma ray energy E' ($\theta_j$) can be determined using Eq. 1. The invention may be configured so that one of the objectives of this embodiment of the invention is to concentrate on only the count rates from gammas scattered within that portion of the shell 165 which is inside the inspected object, onto which portion the modulating unit's field of view is projected, as depicted in FIGS. 5 and 9. As previously discussed, that portion of the isogonic shell 165 is referred to as a virtual isogonic slice. Since only gammas scattered from within these virtual slices carry the signature of flux- and density-distribution within the inspected object, only these gammas are of interest to this embodiment of the invention and therefore are encoded by the modulating unit 120.

The invention determines the values of N local densities (one per NW) within each of J intersections of the virtual projection of the modulator (as viewed from the detector) with J particular isogonic shells 165, whereby these intersections define the virtual isogonic slices of interest. Before calculating the local densities, the invention, in Steps 2-5, identifies the location matrix and intensities of N unmodified single-scattered gamma fluxes. The location matrix is the same for material densities and local gamma fluxes. The term "local" refers to the location at the point of scattering and its associated voxel within the inspected object. The location matrix of the volumetric pixels (voxels) within the inspected object may be defined by the location and shape of the isogonic slices, as well as orientation and design of the modulating unit and detector. These single-scattered gamma fluxes are the time-independent gamma fluxes generated by single Compton scattering inside the inspected object and incident upon the modulating unit on their path towards the detector. After passing through the modulating unit, the magnitude of these fluxes becomes somewhat reduced from that of the incident gammas, and the fluxes become time-dependent upon passage through the oscillating attenuator elements of the modulating unit.

The scattering events and attenuation phenomena within the inspected object are carefully considered using the appropriate equations that characterize them. These events and phenomena enable an unambiguous numerical characterization of the density distribution within the irradiated inspected object.

The scattering formula, shown below as Eq. 2, describes the relationships of variables associated with gamma scattering phenomena, and can be used to calculate the scattered gamma flux. The formula is applicable when no modulation takes place in the paths of the gammas.

$$\Phi_{jq} = (Q^*)(C^*)\left[(\Delta V_P/R^{*2})_{jq}(\rho_{jq}K^*_{jq})(1/H^*_{jq})^2(P_oP')_{jq}\right]P''_{jq} \quad \text{Eq. 2}$$
$$= (Q^*)(K^*_{jq})(\rho P_oP')(P''_{jq})(G^*_{jq})$$

In the above equation:

$\phi_{jq}$=the gamma flux, expressed as the number of gamma photons per second passing through one cm$^2$ of area A* perpendicular to the trajectory of the gammas, at a distance H*, which is the distance between the scattering point (SP) and the center of the area through which gammas pass, anywhere along the distance axis h. The h axis may coincide with the y axis.

$R_{jq}^*$=the distance from the source's center to the scattering point (SP), which is defined—in the manner of other indexed parameters—by the pair of location subscripts jq, where j specifies the scattering slice and its corresponding gamma energy, and q specifies the location of a nodal window within the modulating unit.

Q*=the source strength (in Curies), related to the number of gamma photons emitted per second.

$C^*=(3.7 \cdot 10^{10})/(4\pi)$—a constant, that transforms the unit of Curies into the number of disintegrations per second over the unit solid angle, i.e., the number of gammas emanating from the source per steradian per second.

$\Delta V_P$=the volume of the scattering voxel (volumetric pixel), a small, but finite size volume, that generates a measurable stream of gammas, considered as the average stream value exiting that voxel, and associated with its center-point—which is the scattering point (SP).

ρ=the electron density (proportional to mass-density of material) in the voxel.

K*=the local Klein-Nishina scattering probability (a tabulated physical property). The probability of single-scattering of gamma photons in the Compton process was calculated by Klein and Nishina on the basis of relativistic quantum mechanics, and is discussed by Irving Kaplan in *Nuclear Physics*, Addison Wesley Publ. Co., 2$^{nd}$ Ed., March 1964, which is incorporated by reference.

G*=a composite geometrical parameter, grouping known constants, distances, areas, and volume, appearing in the above equation, corresponding to scattering from SP.

$P_o$=probability that the incident gamma photons from the source will not interact with the attenuating substance of the inspected object during their transit inside the inspected object, prior to scattering.

P'=probability that single-scattered gammas emanating from the inspected object will not interact with the attenuating substance of the inspected object during their transit inside the inspected object, after scattering.

P'''=probability of the non-attenuation of gamma photons resulting from their transit through both walls of the inspected object (upon entering and exiting the object).

The following two equations and the subsequent text define the non-attenuation probabilities $P_o$, P' and P''' appearing in Eq. 3. The abbreviation exp stands for the exponential function (where exp n=e$^n$).

$$(P_o)_{jq}=\exp[-k_o(E_o)\int\rho(r)dr] \quad \text{Eq. 3a}$$

$$(P')_{jq}=\exp[-k'(E_j')\int\rho(h)dh] \quad \text{Eq. 3b}$$

The invention requires integrations from the scattering point (SP)$_{jq}$ to the boundaries of the inspected object, defined as limits of the above integrals, along the r- and h-axis, respectively.

The variables r and h are spatial coordinate axes in the direction of gamma propagation, associated with distances R* and H*, respectively.

$k_o(E)$ denotes gamma energy-dependent specific flux attenuation coefficients for source gammas (of energy $E_o$), expressed as reaction area per electron.

k'(E') is the gamma flux attenuation coefficient for scattered gammas (E'=$E_j$'); here, the subscript; (used with P' and E') refers to a specific value of the energy $E_j$' of scattered gammas. The term k' is expressed in the same units as k.

When the integral(s) in Eq. 3 are replaced by the product of a constant material density and the known path length of gammas through that material, $P_o$ and $P_j'$ become the directly-calculable non-attenuation probabilities for gammas transmitted through such materials, and is denoted by P'''. Thus, the term P''' can pertain to the boundary of the inspected object, a shielding structure, or an element within the modulating unit that is designed to partially block the transmitted gammas.

Eq. 2 can be re-grouped to define the term χ in Eq. 4 below, as a property of the interrogated density field within the inspected object. This property expresses the interrelationship between the field of local gamma fluxes and the field of material densities, needed for carrying out the subsequent density field reconstruction task.

$$\kappa_{jq}=(\rho P_o P')_{jq}=\phi_{jq}/[(Q^*K_{jq}^*)(G^*P''')_{jq}] \quad \text{Eq.4}$$

In addition to the local (point) density, density integrals appearing in Eq. 3 are included in the P-terms of the above group; in a numerical analysis, each such integral can be expressed by an equivalent sum of local densities along a straight line, which is the integration axis.

In summary, the scattering equation, Eq. 2, describes the flux of single-scattered gammas streaming throughout a region having an unknown distribution of mass density, traveling along the h axis, through a unit area at a distance H* from the scattering point. The equation includes known or directly-measurable geometric and physical parameters, such as dimensions and physical properties of the media through which the gammas pass within the inspected volume.

In Step 3, the modulating unit 120 encodes the gamma fluxes by causing a unique periodic oscillation to be imposed on the fluxes within each nodal window of the unit. A steady flux of mono-energetic gammas emanates from the source S, and streams along a group of diverging straight lines which intersect with the virtual slices within the inspected object, as depicted in FIGS. 1, 5 and 9. Numerous gammas will scatter within the inspected object, as well as on portions of the isogonic shells 165 outside the inspected object. These latter extraneous gammas contribute to steady or random background noise signals registered by the detector. In order to eliminate or mitigate their effect, shielding may be used around the source and the detector to block extraneous multiple-scattered gammas. Further, analysis or data processing may be employed to eliminate or calculate the undesired scattered gamma fluxes, as well as the fluxes due to background noise, both categories of which do not originate from directly within the inspected object, and accordingly, cannot be associated with any reconstruction of the inspected object's internal density distribution. Additionally, single-scattered fluxes originating from within the inspected object may be calculated and their points of origin identified; the locations of these points cover all virtual slices, and thereby include all voxels within the volume of the inspected object, which means that the distribution of scattered gamma fluxes and corresponding mass densities within the entire volume of the inspected object can be mapped.

The known gamma flux from the source S irradiates all the virtual isogonic slices within the inspected object. A substantial fraction of these source gammas generates the scattered gamma fluxes, according to Compton's law, described by Eq. 1. The scattering equation, Eq. 2, gives information on the portion of un-modulated scattered gammas that reaches a specific location, e.g., the detector 115. Two observations should be noted:

All of the detected single-scattered gammas coming from each of the virtual slices stacked along their trajectory leave the scattering voxels 144 and stream toward the detector. They are encoded as they pass through the modulator, similar to the situation depicted in FIGS. 5 and 9;

The sub-division of the modulating unit area into N nodal windows-oriented to intercept gammas streaming toward the detector, and the window's virtual projection on the isogonic slices within the inspected object translates into a subdivision of the thin volume of each virtual isogonic slice into N voxels 144, the size of which determines the resolution of the reconstructed density image. FIGS. 5 and 9 illustrate how the modulating unit's pattern of N nodal windows translates into N voxels on each of J virtual slices.

Since only gammas scattered from within virtual slices carry the signature of flux- and density-distribution within the inspected object, only these are of interest to the invention in this embodiment. The field of view defining the projected pyramid (for the rectangular modulating unit), incorporates the entire matrix of N nodal windows (NW). As explained earlier and shown in FIGS. 4 and 6 through 8, a small oscillating attenuator element in each of these windows (or one element shared by two adjacent windows) encodes the gamma flux $\phi_{jq}$ passing through the window, enabling a unique identification of each angular segment of the gamma flux. This temporal encoding modulation differs from window to window. Such an operating arrangement, coupled with the Compton scattering law, provides the basis for the non-invasive determination of density distribution in an object. The Compton scattering law provides information on the scattering angle of single-scattered gammas, which is associated with a particular isogonic slice within the inspected object. That isogonic slice is, in turn, associated with the distance (y or h) from the detector traveled by single-scattered gammas. Additionally, the encoding by the modulating unit provides information on the location of the nodal window's projections on the virtual slices inside the inspected object 105. Thus, the role of the modulating unit is to label the gamma flux that passes through each nodal window of the modulating unit by a window-specific periodic attenuation of the gamma flux. The un-modulated single- and multiple-scattered fluxes, propagating externally to the virtual projection of the modulator or the inspected object (as viewed from the detector), as well as any other detected constant or randomly fluctuating background radiation, are eliminated by the integration that takes place in Step 8 of FIG. 10B.

In any particular nodal window of the modulating unit, the attenuation function imposed on the gammas by a modulating attenuator element can be described by the periodic function a(q, t), with q denoting the location of the element (the nodal window's attenuator) within the modulating unit, and t being real time.

For any energy $E_j'$ of scattered gammas, the single-scattered gamma flux incident upon NW #q, constant in time, as a specific expression of Eq. 2, is denoted by $\phi_{jq}$. Along its propagation direction, the periodic transient flux exiting the same nodal window is equal to the product of the steady incident flux and the relative transmission area of the nodal window, where the relative transmission is a function of time denoted by a(q, t), and is expressed by Eq. 5 below. The term "relative" means that the gamma transmission is normalized to that which would occur if the attenuation caused by the nodal window was zero (for the case of no gamma-attenuating material present in the nodal window). The partial attenuation according to the function a(q, t), which is a physical modulating function, is represented by the equations shown below.

$$a(q, t) = S_q^* + A_q \sin(\omega_q t + p_q) \quad \text{Eq. 5a}$$

$$= S_q^* + A_q[(\sin \omega_q t)(\cos p_q) + (\cos \omega_q t)(\sin p_q)] \quad \text{Eq. 5b}$$

$$= S_q^* + (A_q \cos p_q)\sin \omega_q t + (A_q \sin p_q)\cos \omega_q t \quad \text{Eq. 5c}$$

$$= S_q^* + A_q' \sin \omega_q t + A_q'' \cos \omega_q t \quad \text{Eq. 5d}$$

In Eqs. 5, $S_q^*$ is referred to as the shift constant since it can move the a(q, t) function along the time axis, while $A_q$ is the amplitude of the a(q, t) function; $\omega_q$ is its frequency and $p_q$ is the delay, or phase-angle corresponding to the time delay $p'=p/\omega$. A variation in frequency, of course is inherent in frequency modulation (FM). The terms $A_q'$ and $A_q''$ are the combined amplitudes, formed by the product of $A_q$ with the indicated trigonometric functions of the phase angle. The structure of Eq. 5c shows that phase modulation (PM) is mathematically equivalent to a dual-amplitude modulation (AM). As an observation of Eq. 5a: when seeking an efficient and simplified design and operation of the modulation unit, the invention can be configured to work with more than one kind of modulation (such as FM or PM, rather than solely with AM), or designed to combine all three of these modulation modes in various ways.

After the completion of the modulation-encoding process performed in Step 3, in step 4 of FIG. 10A, two kinds of fluxes travel toward the detector—(1) those fluxes from single-scattering within the inspected object, and (2) fluxes unrelated to the inspected object density distribution.

Thus, in Step 4 of FIG. 10, the invention observes the single-scattered gammas that emanate from any representative jq-th voxel (from the j-th slice in the inspected object, and passing through the q-th NW of the modulating unit 120) before reaching the detector/spectrometer. The symbols below that are used in subsequent equations represent the following quantities:

$\phi_{jq}$=the steady flux of single-scattered gammas having energy $E_j'$, incident on the q-th nodal window of the modulating unit; Eq. 2 also addresses such a flux;

a(q, t)=the time-dependent attenuation function expressed by Eq. 5, imposed on the gamma flux incident on the modulating unit's nodal window #q;

$A_D$=the geometrical unobstructed area of the detector as seen through the nodal window #q;

$\alpha_q$=the angle of incidence of the gamma flux (measured between the trajectory of the gammas and the surface vector of the detector. This angle is zero for gammas arriving perpendicular to the plane of the areal surface of the nodal window #q.

The subscript q that encompasses indices I and k (as shown in FIG. 10) may be used in three respects: 1) to indicate those fluxes of gammas scattered from any among J isogonic slices within the inspected object, and pass through NW #q of the modulating unit; 2) to indicate a unique attenuation function a(q, t) of the $q^{th}$ NW; and 3) to specify the angle of incidence of the gamma flux at NW #q, as will be discussed shortly.

The following Eqs. 6a and 6b describe the periodically varying gamma stream having photons of energy $E_j'$ at the exit of window #q of the modulating unit, that reaches the detector due to the convergence of paths depicted in FIG. 9.

The relationship among the important count-rate and flux-related magnitudes may be demonstrated by the following example. The unknown constant local flux of single-scattered gammas $\phi_{jq}$, enters the modulating unit's nodal window. These gammas exit that nodal window at a somewhat reduced intensity given by the quantity $[\phi_{jq}a(q, t)]$. That term, when multiplied by the detector's area $A_D$, expresses the stream of modulated gammas leaving NW #q of the modulating unit and traveling in the direction of the detector/spectrometer. That product has to be multiplied by the detector efficiency $\eta_{jq}$. Dual subscripts j and q are used with this detector efficiency term to indicate its dependence on the gammas' energy, and on the nodal window's location in the modulating unit, respectively. That location also affects the incidence angle $\alpha_q$, of gammas arriving at the detector. Since the cosine of that angle specifies the fraction of the arriving gammas that will enter the detector, the following equation, encompassing all the listed parameters, expresses the detector count rate $D_{jq}'$, which corresponds to the local scattered gamma flux $\phi_{jq}$ and local mass density $\rho_{jq}$.

$$D_{jq}'=[\phi_{jq}A_D\eta_{jq}\cos\alpha_q][a(q, t)] \quad \text{Eq. 6a}$$

which equation contains the group $$[\phi_{jq}A_D\eta_{jq}\cos\alpha_q]=\Phi_{jq} \quad \text{Eq. 6b}$$

In Step 5 of FIG. 10B, the detector/spectrometer output signal is fed into the MCA 135 which sorts the detected signal pulses into bins, each corresponding uniquely to a particular scattered energy of the detected gammas. The invention can be configured so that a selection may be made in terms of bin width $\Delta E_j$, which defines energy resolution; the number of bins, and the full range of energy values to be covered may also be selected. In this application, the count rate $D_j'(t)$ of each bin varies periodically with time because gamma fluxes undergo temporal modulation during their passage through the nodal windows of the modulating unit.

Based on its constituents, the symbol $\Phi_{jq}$ represents the detector's response to unmodulated single-scattered gammas passing through any particular fully open nodal window #q. Once the value of such a response term is numerically determined, the matrix of flux values $\phi_{jq}$, that the system seeks, can be calculated from the matrix of these $\Phi_{jq}$ values defined above, since other parameters in Eq. 6b are known.

When $\Phi_{jq}$ is used in Eq. 6a, a convenient working form becomes:

$$D_{jq}'=\Phi_{jq}a(q, t) \quad \text{Eq. 6c}$$

The known function a(q, t) is retained as a term separate from $\Phi_{jq}$ within the $D_{jq}'$ term so that the invention can use the Fourier Transform involving the product $[a(q, t)\cdot b(n, t)]$ in the course of data processing.

In order to calculate the $\Phi_{jq}$-matrix, one proceeds by considering all the JN values of detector count rates corresponding to local gamma fluxes incident on the nodal windows of the modulating unit. Thus, the data processing may start from the measurable information, namely the sub-total count rates, such as $D_j$, which are registered in the $j^{th}$ bin of the detector/spectrometer's MCA. That count rate, through $D_{jq}'$, encompasses the effects of all $\Phi_{jq}$ contributions. The relation of $D_j$ with its constituents, $D_{jq}'$, and with the total count rate $D^*$, (that is formed by the summation of all J sub-total count rates $D_j$), is given by the following two equations:

$$D_j = \sum_{q=1}^{N}\Phi_{jq}a(q, t) + \sum_{q=1}^{N}\Phi_j' = \sum D_{jq}' + \Phi_j' \quad \text{Eq. 7}$$

$$D^* = \sum_{j=1}^{J}D_j \quad \text{Eq. 8}$$

The $2^{nd}$ summation term in Eq. 7 is expressed by the abbreviated symbol $\Phi_j'$, that encompasses gamma fluxes $\phi_j'$ of energy $E_j$, which are traveling toward the detector and are unrelated to the inspected object's internal density distribution. These gamma fluxes might undergo multiple or single scattering wherein at least one of the scattering events occurs external to the inspected object; some of those fluxes are due to background radiation. The physical reality is that the group of registered gammas, denoted by $\Phi_j'$, contains fluxes that may have been scattered randomly one or more times in various objects and at various distances from the detector. They include the following radiation components:

un-modulated single-scattered gammas from portions of the isogonic shell external to the isogonic slices (external to the inspected object);

multiply-scattered (modulated and un-modulated) gammas, as well as background radiation of various origins.

All of the radiation components listed here may have an energy $E_j'$, and therefore will be registered in the $j^{th}$ energy bin of the MCA 135. However, none of the undesired components yields useful information on the inspected object's density field. All of these signals have no systematic time-variation; but their magnitude could either be measured separately or calculated. In the latter option, they can be subtracted from the bin-registered count rate $D_j$; also they could be mathematically eliminated during the data analysis. The recommended data processing incorporates application of the Fourier Transform.

In condensing information given earlier on the modulation of fluxes, it is observed that, as a consequence of the modulating unit's design, directional orientation, and operation, gamma fluxes incident upon nodal windows of the modulating unit may become appropriately encoded while passing through the modulating unit's nodal windows; such encoding makes possible the determination of the following:

In the first operation, the $\Sigma D_{jq}'$ summation term, seen in Eq. 7 is important for further data processing, because it includes all the useful single-scattered gamma fluxes— contained in the $\Phi_{jq}$ terms—pertaining to the scattering occurring in the $j^{th}$ isogonic slice within the inspected object. These slices are important because only detected gammas which scatter once within such slices carry the signature of the gamma flux and mass density distribution within the inspected object. Also, as indicated earlier, J of these virtual slices fill the volume of the inspected object.

Individual count rate-related terms are $\Phi_{jq}$, from Eqs. 6b and 7, which terms were included within the directly-measured $D_j$ term. $\Phi_{jq}$ corresponds to gamma flux components $\phi_{jq}$ incident on the modulating unit's nodal windows, where each component of gamma flux is associated with a particular jq voxel of the inspected object. This second operation of determining all (N) of the needed local magnitudes $\Phi_{jq}$ is expanded to all J isogonic virtual slices, resulting in the determination of (JN) such terms, covering the entire inspected object's internal scattered gamma flux-distribution. This distribution is subsequently converted into the three-dimensional mass (density) distribution and a corresponding computerized visual image.

In Step 5 of FIG. 10B, the set of output signals from the MCA are split into J sets of signals. Because of the Compton scattering energy-angle relationship defined in Eq. 1, the sorting of output signals from the detector based on their energy also becomes a sorting by scattering angle θ. In the MCA bin #j, the energy $E_j'=E'(\theta_j)$ of scattered gammas is associated with the registered gamma counts $D_j(t)$ in that particular energy bin.

The count rate registered in each energy bin should be processed N times (where N is the maximum value of q, thus defining the total number of nodal windows in the modulating unit). Therefore, N is also equal to the number of unknown scattered fluxes to be determined (emanating from N voxels in the j-th isogonic slice of the inspected object); these fluxes are incident upon the modulating unit. Consequently, as illustrated in Steps 6 and 7 of FIG. 10B, each of the J sets of $D_j(t)$ signals is further split into N equal signals by a signal splitter, and sent to N multiplying black boxes shown in Step 7. For the $1^{st}$ signal-splitting level performed in Step 5, input signals for each signal splitting box differ from input signals for other signal-splitting boxes. However, for each particular ($j^{th}$) signal-splitting box of Step 6, all the split signals exiting any of these individual boxes are identical among themselves. The latter group of equal split signals from the j-th box, of course, differs from groups of signals exiting other similar boxes where the subscript j has a different value. Such signal-splitting enables the concurrent processing of all measured counts. While the following analysis and derivations are outlined based on a representative $j^{th}$ value of the energy of scattered gammas, they are fully applicable to any other energy value of scattered gammas.

In Step 7, a set of time-varying b(n, t) sine functions are electronically generated by a function generator 182. In this stage of the process, the invention introduces a new dimensionless transform-function, denoted in its general form as $F_b(n, t)$. The term "transform" refers to this function's role in performing the Fourier Transform that will be outlined below. The transform function has to be selected to match the modulating function a(q, t), expressed in Eq. 5, as is done by the example of a specific function $F_b(n, t)$, given by Eq. 9.

$$b(n,t)=B_n^* + B_n' \sin \lambda_n t + B_n'' \cos \lambda_n t \quad \text{Eq. 9}$$

The above function b(n, t) mimics the a(q, t) function from Eq. 5. The transform function b(n, t) serves as a time-dependent multiplier of the detector output signal $D_j(t)$, as will be shown later in Eq. 11. The above transform function represents the n-set (where n is a positive integer, taking values from n=1, to n=N) of periodic oscillations, mathematically similar to the q-set of the a(q, t) functions. The gamma flux modulating functions a(q, t) are physically generated by the time-dependent attenuation of the modulating unit. On the other hand, transform functions b(n, t) are electronically-generated digital functions. One noted difference between the a(q, t) functions and the b(n, t) functions is that in the b(n, t) function, there is no need for a separate reference to the phase-lag addressed in the earlier discussion of the a(q, t) function in Eq. 5. Also, within the b(n, t) function an operator can choose and vary the values of parameters such as the shift constant B* and amplitudes B' and B'' by computer control (in some solution procedures, one or more of the listed B-coefficients might be chosen to be zero or one). To the contrary, the operator can vary the hardware-related A-parameters of the a(q, t) function only by changing the nodal window and attenuator configuration of the modulating unit.

The circular frequencies $\omega_q$ and $\lambda_n$ appearing in functions a(q, t) and b(n, t), respectively, are defined to assume only discrete values, appropriate for the application of the Fourier Transform. These frequencies obey the relationships defined in Eq 10:

$$\omega_q = \pi q^*/T, \text{ with } q^* = f_q(q) \text{ or } f_i(i) \text{ incorporated in } a(q, t) \quad \text{Eq. 10a}$$

$$\lambda_n = \pi n^*/T, \text{ with } n^* = f_n(n) \text{ with } \lambda_n, \text{ incorporated in } b(n, t) \quad \text{Eq. 10b}$$

Also, $n^*$ can be expressed as:

$$n^* = f_i(i) \text{ or } n^* = f_q(q) \quad \text{Eq. 10c}$$

The use of functions $f_i$, $f_n$, and $f_q$, as choices in the group of Eqs. 10 depends on the analysis approach selected, as will be shown in Steps 8 and 9 of FIG. 10B. The parameters (i, n, n*, q and q*) shown above are positive integers; their selected values also depend on the analysis approach. For i, the maximum value is I, while for both n and q the maximum value is N. T is the half-period of the oscillation of the slowest moving attenuating element in the modulating unit (for which element q*=1).

In Step 7, the MCA output is multiplied by the $2^{nd}$ set of temporal functions b(n, t), generating a product [Φ(q)·a(q, t)·b(n, t)]. Both of these functions—a(q, t) and b(n, t)—are chosen to be periodic (sine or cosine) functions. In this and the following analytical operations, depicted by Eqs. 11 through 13 below, products of functions, including a(q, t) and b(n, t) are formed and integrated over time. Referring to FIG. 10B, the small black boxes (shown in Step 7) represent electronic devices in which digital signals from the J signal splitting boxes 180 are joined by digital signals from the b(n, t)—function generator 182. In these black boxes, the two signals are multiplied with each other. In other words, the time-dependent MCA output signal $D_j(t)$ from energy bin #j is multiplied in each branch by one electronically-generated function b(n, t), forming a combined signal. In the next parallel branch, the same signal $D_j(t)$ is multiplied by another function b(n, t) with a different set of values for n-dependent and n-subscripted parameters introduced in Eq. 9.

Since both factors [$D_j(t)$ and b(n, t)] of the product term are functions of time, their product-function is also time-dependent. The integration of the product function, in Step 8, constitutes a version of the Fourier Transform. These products are integrated over a period of time, as in a Fourier Transform, to eliminate signals other than those generated by the single-scattered gamma photons originating in the inspected object, and modulated by the modulating unit. According to Eq. 13 in Step 8 of FIG. 10B, such product functions are then integrated by an integrator 184 over a selected measurement-time period that may be equal to T, or preferably any integral multiple of 2T. Such an integration is an important step in the subsequent decoding of the gamma fluxes, wherein their original encoding was accomplished within the modulating unit by the time-dependent attenuation function a(q, t).

The detector count rate, as its response to a modulated flux of local single-scattered gammas, is given by Eq. 6a. The corresponding flux group from Eq. 6b of scattered gammas had a constant magnitude $\Phi_{jq}$ (independent of the modulation), and the gammas comprising that scattered flux have modulation-independent energy $E_j'$. The count rate $D_{jq}'$ is also expressed by Eq. 6c, which is the detector response to single-scattered gammas of energy $E_j'$ incident on the $q^{th}$ NW.

Using Eq. 7 for $D_j(t)$ and Eq. 9 to express b(n, t), the product [$D_j(t)$ b(n, t)] may be expressed as:

$$D_j(t) \cdot b(n, t) = D_j(t) \cdot [B_n^* + B_n' \sin \lambda_n t + B_n'' \cos \lambda_n t] \quad \text{Eq. 11}$$

Substituting the expression for $D_j(t)$ given in Eq. 7 yields:

$$D_j(t) \cdot b(n, t) = \left[ \sum_{j=1}^{N} \Phi_{jq} a(q, t) \right][b(n, t)] + [\Phi_j'][b(n, t)] \quad \text{Eq. 12}$$

The $\Phi_j'$ term in Eq. 12 was expressed earlier in Eq. 7, as being without a time-variation imposed by the modulator. Since it is constant in time, upon integration within limits specified in Eq. 13a below, that term is eliminated, and therefore does not appear in Eq. 14. It should be noted that, while all terms in Eq. 12 become known or eliminated, only one category of terms remains unknown—the gamma flux terms $\Phi_{jq}$. In order to determine each of these terms, the procedure is as follows: first, Eq. 12 is integrated between the selected finite integration limits (0 and 2T), as expressed by Eq. 13a below, which applies to any value of j. With functions a(q, t) and b(n, t) substituted in Eq. 12 by their expressions in Eq. 5d and Eq. 9, respectively, the resulting Eq. 13a reads as follows:

$$\int_0^{2T} D_j(t) b(n, t) dt = \quad \text{Eq. 13a}$$

$$\sigma_{jn} = \int_0^{2T} D_j(t)[B_n^* + B_n' \sin\lambda_n t + B_n'' \cos\lambda_n t] dt$$

The term $\sigma_{jn}$ is the result of the Fourier Transform of the count rate from bin #j, encompassing gamma fluxes having an energy associated with that bin.

Now, substituting the expression for $D_j(t)$ in the above integral by using Eq. 12 and using $B_n^* = 0$ (for simplification) for each particular value of n in the b(n, t) function, results in:

$$\sigma_{jn} = \int_0^{2T} \left\{ \left[ \sum_{q=1}^{N} (\Phi_{jq})(S_q^* + A_q' \sin\omega_q t + A'' \cos\omega_q t) + \Phi_j' \right] \cdot \right.$$

$$\left. [B_n' \sin\lambda_n t + B_n'' \cos\lambda_n t] \right\} dt \quad \text{Eq. 13b}$$

Since the quantity $\sigma_{jn}$ as expressed in Eq. 13a is the integral of known functions within a selected finite limit of time (the duration of the inspection measurement wherein gamma counts are recorded), the symbol ($\sigma_{jn}$) represents a known, calculated number. For a defined set of recorded data, that number depends only on the values of coefficients and frequencies associated with the parameters q and n, the former within the function a(q, t) and the latter within the b(n, t) function that is given by Eqs. 5 and 9, respectively. On the other hand, since N unknown constant groups $\Phi_{jq}$ (proportional to NW-incident scattered fluxes) appear in Eq. 13b, when n is varied from 1 to N, each value of n generates an equation of the type Eq. 14 that is linear in regard to $\Phi_{jq}$. In Step 9 of FIG. 10B, the output of the integrators 184 results in a system of N linear algebraic equations, providing N values of the local gamma flux at each of the N voxels within the j-th isogonic slice of the inspected object. In this manner, the decoding of the modulated fluxes is achieved in all (JN) voxels of the inspected object. When equations of the Eq. 14 type are mutually independent, they represent a system of linear algebraic equations 186 which can be solved for the unknown incident fluxes by an equation solver.

With the integrations performed, as indicated in Eq. (D-5b), the result reads:

$$\sigma(j, n) = \quad \text{Eq. 14}$$

$$\sigma_j(T) = \left\{ \sum_{q=1}^{N} \left[ \Phi_{jq} \int_0^{2T} a(q, t) b(n, t) dt \right] = \left\{ \sum_{q=1}^{N} [(\Phi_{jq})(TC_{nq})] \right\} \right.$$

where:

$$C_{nq} = (A_q' B_n' + A_q'' B_n'')$$

In the above equation, all nodal windows of the modulating unit 120 are included through the indicated q-summation, starting with q=1 and ending with q=N, since N is the total number of these windows in the modulating unit. The shape or form of the nodal windows is not a condition for achieving a solution.

Eq. 14 above represents in a condensed form, a system of N linear algebraic equations, utilizing values of the parameter $\sigma(j, n)$ for each value of the index n (which starts with the value 1 and ends with N), while the span of values of the index j is from 1 to J.

The solution of linear algebraic equations (for a variety of design and operation options of the modulating unit) is indicated in Step 9 of FIG. 10B. The application of Eq. 14 for a system with N unknown fluxes results in a system of N independent linear algebraic equations and is illustrated by Eq. 15 shown in FIG. 11. For any particular chosen $j^{th}$ energy of scattered gammas, that equation represents, in an abbreviated manner, the complete set of N linear algebraic equations, with the same number N of unknown values of the local single-scattered gamma flux group $\Phi_{jq}$ Eq. 15, as shown in FIG. 11, results from expanding Eq. 14 for a given j-value, but with various values of n and q, yielding the illustrated set of N linear algebraic equations. This system of equations can be solved for all values of the parameter $\Phi_{jq}$ that is (according to Eq. 6b) proportional to the value of the local gamma single-scattered flux—eventually resulting in a determination of flux and mass density distribution within the inspected object.

In Step 9 of FIG. 10B, the field of single-scattered gamma fluxes is determined for the entire inspected object—by combining solutions of J systems of equations such as Eq. 15 into a numerically-determined (known) spatial matrix. Subsequently, in Step 10 of FIG. 10B, the density field is reconstructed within the inspected object by converting the local gamma fluxes into densities. It is noted that the detected signal incorporates the cumulative effect of local scattering and two sets of density-related attenuation: 1) along the gamma beam path (axis) from the source to the scattering point, and 2) along the gamma path from the scattering point to the detector. Each attenuation depends on the average density distribution along their respective axes. That distribution, as it becomes known, enables the image reconstruction using this invention.

Density Field Reconstruction

In step 10 of FIG. 10B, the density field within the inspected object is reconstructed by a three-dimensional density field reconstructor 188 by converting the local gamma fluxes into local densities. The two average densities appearing in Eqs. 2 and 3, in turn, depend on the unknown density distribution along their respective axes. Consider any material inside the inspected object. An unambiguous correspondence exists between the three-dimensional distribution of local single-scattered gamma fluxes and the three-dimensional distribution of material densities that represent the density image. The term "local single-scattered gamma fluxes" pertains to gamma photons originating within voxels associated with scattering points within the inspected object. The unambiguous correspondence between gamma flux and material density is illustrated in Eqs. 2, 3, and 4, in which the field parameter κ—written with the subscript P (denoting point of scattering) instead of the indices jq—combines several terms. The rewritten Eq. 4 reads:

$$\kappa_P = \phi_{jq}/[(Q^*K_{jq}^*)(G^*P'')_{jq}] = \rho_P P_o P_P' \qquad \text{Eq. 16}$$

At the beginning of the field-conversion effort, the JN numerical values of the following parameters are known:
the terms $\Phi_P$, from Eqs. such as Eq. 15 (FIG. 11)
local fluxes $\phi_P$ which are related to $\Phi_P$ by Eq. 6b, and
the parameter $\kappa_P$, calculated from the fluxes $\phi_P$ and known parameters, using Eq. 16.

Having available the necessary number of numerical values of the parameter $\kappa_P$, Eq. 18 must be applied (JN) times, which number was shown to be the total number of unknown local densities $\rho_{jq}$, as shown in Eq. 17 below. In Eq. 17, the flux-to-density field conversion becomes simpler when the integrals included in the probabilities of non-attenuation (from Eq. 3) are expressed as sums of local, voxel-related densities $\rho_{jq}$.

$$\chi_P = [\rho_P]/\exp\left\{\left[k_o \sum_{j=j_S}^{j=j^*} (\rho_{jq})_o \Delta r\right] + \left[k_P' \sum_{j'=j_D'}^{j'=j^*-1} (\rho_{j'q'})' \Delta h\right]\right\} \qquad \text{Eq. 17}$$

The above equation incorporates the field parameter κ and the local density ρ, the latter in two functional forms: as $\rho_P$ and summed-up values $\rho_{jq}$. In further derivations and figures, the directions $r_q$ and $h_q$ will be often denoted only by q and q' respectively.

Equation 16 illustrates how to calculate numerical values of $\kappa_P$ at any of the scattering points P, associated with gamma flux values $\phi_{jq}$, which are already numerically determined at all the scattering points within the inspected object. Other parameters and variables with the symbol and subscript (P), including the density $\rho_P$, also pertain to scattering points 122 in FIGS. 1 and 12, identified by the symbol SP or P. The cited coordinates and other parameters are listed appropriately and indexed/subscripted or otherwise marked; they are also shown in FIG. 12.

Figure 12:
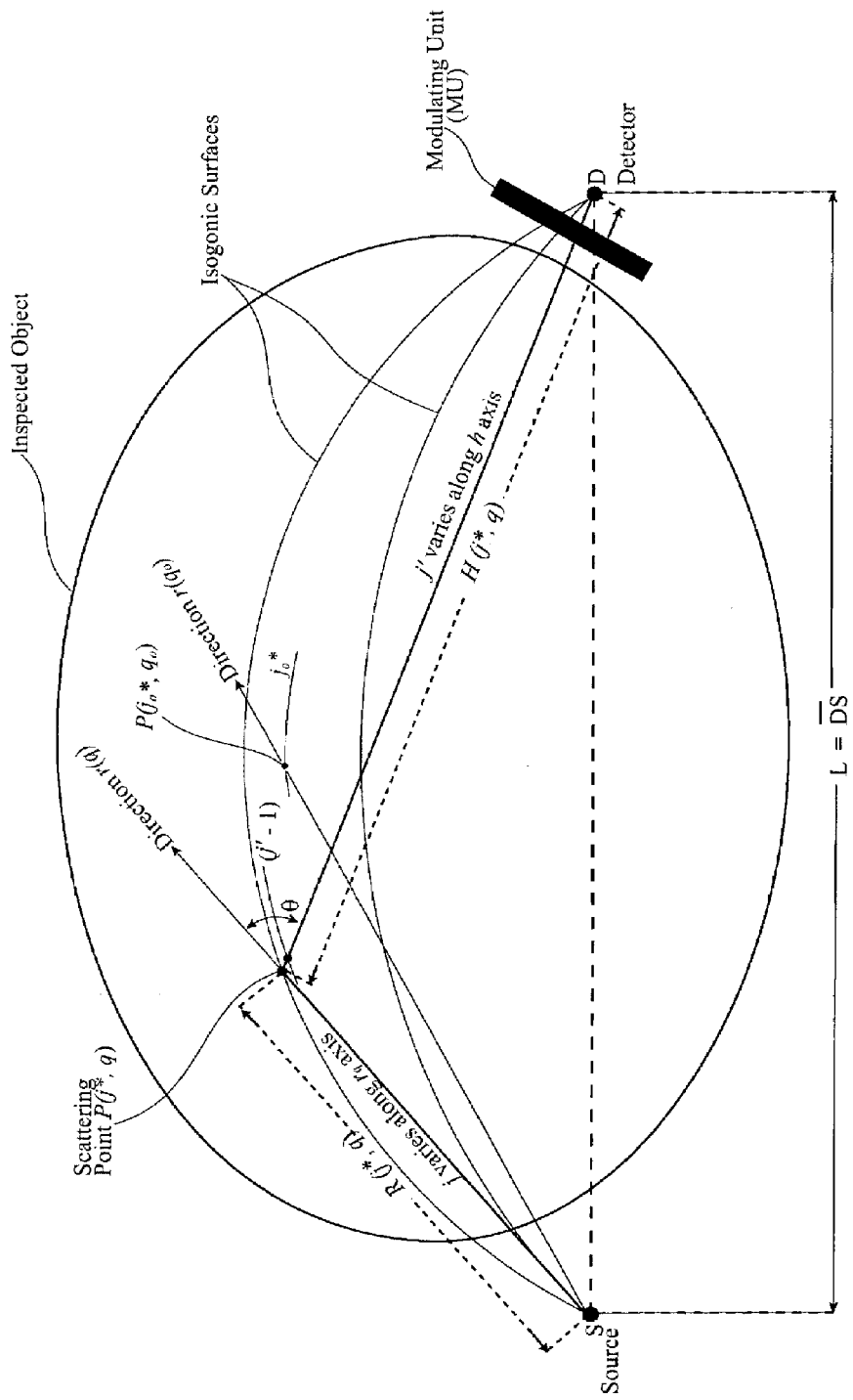
FIG. 12 illustrates parameters relating scattered gamma photon flux to mass density within the inspected object.

The deployment of the key components of the invention (source, modulator, and detector) shown in FIG. 12 places the modulator between the inspected object and the detector. The analysis provided below for reconstructing the mass density within the inspected object is based on this arrangement. An alternate arrangement of the key components would be for the modulator to be placed between the source and the inspected object. The data analysis for that alternate arrangement is analogous to the first arrangement and utilizes the same input data, mathematical solution, and data processing.

As illustrated in FIG. 12, the location of the point P in a plane cross-section through the inspected object is defined by two indices (j* and q), employed as follows: The index j* defines the particular isogonic slice on which point P is located (the slice being associated with the energy $E_j'$ of the scattered gamma), while q axis—by intersection with the j* curve—defines the location of point P on the isogonic slice. That location (inside the inspected object) is associated with the virtual projection along the corresponding axial direction #q onto the isogonic slice, as observed from the point S (Refer to FIG. 12. The coordinates (j, q), and their above-listed specific values (e.g., j*, j', $q_D$, and q') utilized in FIG. 12 and in Eqs. 17 and 18, help illustrate how gamma photons that are scattered from the isogonic slice #j*, pass across a number of other isogonic slices (associated with the variable subscript j') on their way from point P while traveling in the direction h(q') toward the modulating unit and the detector D. Regarding other notations in Eqs. 17 and 18 to follow, $k_o$ pertains to the attenuation of gammas having a source energy $E_o$, as in Eq. 3a, and $k_P'$ is the attenuation probability, depending on the energy $E'(\theta_P)$ of scattered gammas, addressed earlier in Eq. 3b.

In Eq. 17, the subscript "o" with the parenthesis around the density term $\rho_{jq}$ of the first summation, and the prime symbol with the second summation, have the meaning associated with these symbols when specifying $k_o$ and k', as explained earlier in Eq. 3. In Eq. 17, these two symbols signify that different sets of local densities—$(\rho_{jq})_o$ and $(\rho_{jq})'$—are summed up along two distinct axes, the r-axis (from the source), and the h-axis (from the SP), respectively. Such a distinction applies to real systems, with non-uniform density distributions, wherein densities may vary differently along these two axes. Thus, for the modulator unit located near the detector, in accordance with FIG. 12 and the explained application of subscripts j and q, it is evident that j varies along the r-axis (direction q for the primary gammas) in a different way from the variation of j' along the h-axis that is denoted by h(q') for the scattered gammas. Thus, Eqs. 17 and 18 can be so formed to cover all JN scattering points in the inspected object, thus enabling the calculation of all JN local densities at these points, based on the JN local fluxes that were already calculated.

In order to obtain a numerical solution, Eq. 17 is converted to the logarithmic form shown below as Eq. 18, to simplify the numerical operations by working with a linear form of most of the unknowns rather than with their exponentials:

$$\ln\chi_P = \ln\rho_P - \left\{\left[k_o \Delta r \sum_{j=j_S}^{j=j^*} (\rho_{jq})_o\right] + \left[k_P' \Delta h \sum_{j'=j_D'}^{j'=j^*-1} (\rho_{j'q'})'\right]\right\} \qquad \text{Eq. 18}$$

In multiple applications of the above equation, the subscript P pertains to values of κ, ρ, and k' at coordinates (j*, q) of point P. There are JN total variations of the two coordinates of the points P in the volume of the inspected object, wherein each of the points P, identified by the coordinates (j*, q) represent a specific voxel. Thus, the total number of voxels under consideration within the inspected object is also equal to the product JN.

In order to transform the flux field of scattered gammas into a mass density field, Eq. 18 has to be solved for the local densities in JN voxels (i.e., at JN points P). The sequence for the successive selection of points P, i.e., for conducting the numerical calculations is left to the user's discretion. Among available choices, the points P along the inspected object's isogonic slices can be varied, or the user can start in one section of the inspected object (moving spirally or otherwise inward or outward), and then switch to other sections; or the user may conduct the numerical operations by other paths and sequences. Since the complete system of JN equations is simultaneously solved, the described field reconstruction method need not be applied in steps, such as to a succession of cross-sections of the inspected object (as used in image reconstructions for CAT and MRI applications), which require multiple axial positionings of the measuring system relative to the inspected object.

A portion of the densities $\rho_{jq}$ and $\rho_{j'q'}$ is summed-up in each local application (at each scattering point P) of Eq. 18. As in FIG. 12, with the variation of locations of the point P, at least one of the two axes (r and h) also vary. Therefore, a limited but varying number (batch) of densities $\rho_{jq}$ is included in each direction of the gamma path through the inspected object, for each application of Eq. 18. The contents of such batches of densities differs for different scattering points since each pair of axes r and h cover only a fraction of the inspected object's volume. The number of densities in each batch is less than JN, but each particular density out of their total number JN appears in one or more batches, i.e., one or more equations of the type Eq. 18. Accordingly, the user has available a solvable system of JN independent, albeit non-linear, equations of the form shown by Eq. 18. Therefore, the established system of JN equations can be used for the numerical determination of the same number JN of unknown local densities. It is noted that the form of Eq. 18 is very similar to that of a linear algebraic equation, except for only one logarithmic term.

Eq. 18 may be written as the system of JN equations shown below, using the subscript scheme from FIG. 12. The subscript P is replaced by the actual pair of subscripts (j*, q) defining a three-dimensional matrix of scattering points, since q is a two-dimensional index. The following equation set is designated as Eq. 19.

For (j*, q)=(4, 1) and q'=5', at point A of FIG. 12 yields:

$(ln\kappa)_{4,1} = ln\rho_{4,1} - k_o\Delta r\rho_{1,1} - k_o\Delta r\rho_{2,1} - k_o\Delta r\rho_{3,1} - \ldots$
$-k'\Delta h\rho_{3,5'} - k'\Delta h\rho_{2,5'} - k'\Delta h\rho_{1,5'}$  Eq. 19a In like manner, for (j*, q)=(5, 1) and q'=6', at point B yields:

$(ln\kappa)_{5,1} = ln\rho_{5,1} - k_o\Delta r\rho_{1,1} - k_o\Delta r\rho_{2,1} - k_o\Delta r\rho_{3,1} - \ldots$
$-k'\Delta h\rho_{4,6'} - k'\Delta h\rho_{3,6'} - k'\Delta h\rho_{2,6'} - k'\Delta h\rho_{1,6'}$  Eq. 19b And for (j*, q)=(6, 1) and q'=7', at point C yields:

$(ln\kappa)_{6,1} = ln\rho_{6,1} - k_o\Delta r\rho_{1,1} - k_o\Delta r\rho_{2,1} - k_o\Delta r\rho_{3,1} - \ldots$
$-k'\Delta h\rho_{5,7'} - k'\Delta h\rho_{4,7'} \ldots - k'\Delta h\rho_{1,7'}$  Eq. 19c The sub-set of Eqs. 19 above illustrate the relationship of the density parameter with other variables (that are known or can be measured or calculated) along the q=1 axis and for any values of j* and q'. Staying with one q-value, j* is varied between its extreme values inside the inspected object.

Now, in the next sub-set of equations, j*=4, but the r(q)-axis is moved to the left where q=2, so that the (j*, q) intersection at point E is along the direction h(q') from the detector, with q'=5'. In this way, point F is identified by j=3 and q=1, having the same coordinates j=3 and q'=4'.

Continuing, for (j*, q)=(4, 2) and q'=4', for point E yields:

$(ln\kappa)_{4,2} = ln\rho_{4,2} - k_o\Delta r\rho_{2,1} - k_o\Delta r\rho_{2,2} - k_o\Delta r\rho_{3,2} - \ldots$
$-k'\Delta h\rho_{3,4'} - k'\Delta h\rho_{2,4'} - k'\Delta h\rho_{1,4'}$ For the new value of q=(2, j*) is to be varied further, analogous to its variations for q=1.

Figure 13:
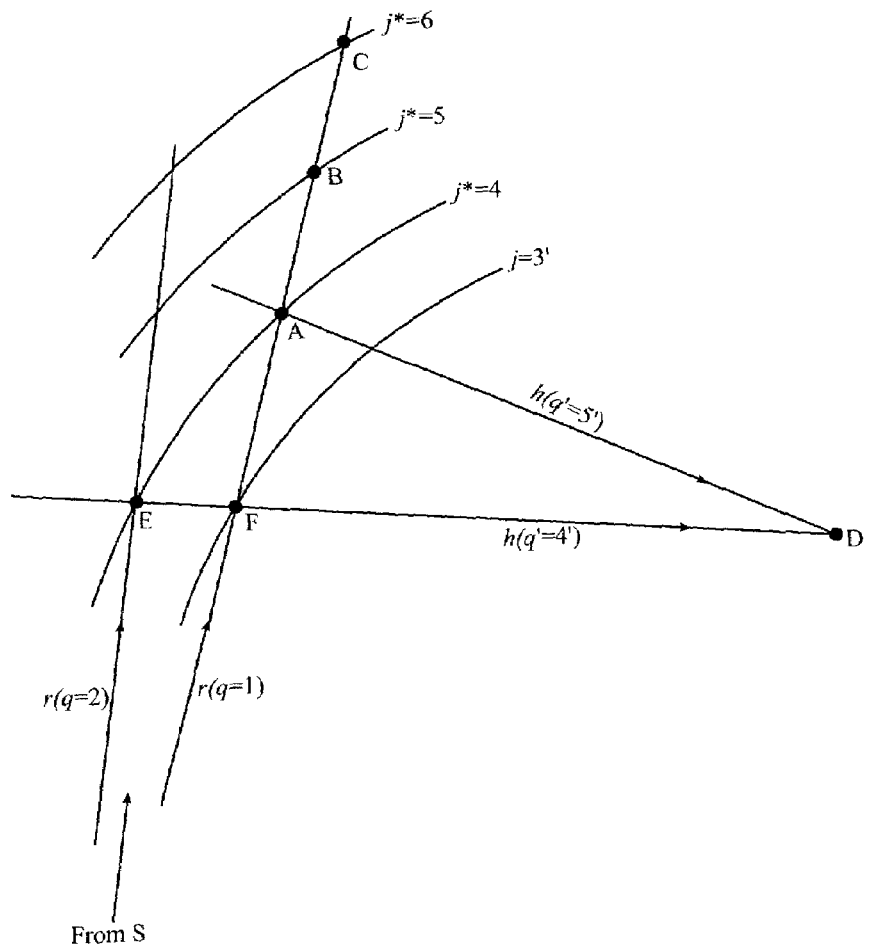
FIG. 13 illustrates parameters used in density reconstruction.

Referring to the third term in the top equation (for point A) of the above set of equations, and the fifth term in the last equation (for point E) of the set, according to FIG. 13, $\rho(j, q) = \rho(3, 1) = \rho(3, 4')$ since both notations indicate point F. The different second index is used to distinguish between summation along the r(q) and h(q') axes, which axes bear numbers (r=1) and q'=4'), respectively. The importance of the same density appearing in the format illustrated above is in its different multipliers: the term $k_o\Delta r$ is not equal to the term $k'\Delta h$. This difference assures the non-proportionality of the rows and columns in the system of equations—a necessary condition for the system of equations to be solvable. There are several approaches available for solving the set of JQ equations, as outlined below:

Approach I—Since the Eq. 19 set has JN independent equations containing the same number of unknowns, despite its mixed (algebraic+logarithmic) form, that set of equations has only one set of JN values of $\rho$ as its exact solution. Any set of JN equations (whether algebraic or transcendental) with JN unknowns is solvable. Eq. 19 consists of mostly algebraic terms; only the first term (the logarithmic term) is transcendental. The set of equations may be solved algebraicly to a first approximation, particularly since the $(ln\rho)$-values are an order of magnitude smaller than the $(\rho)$-values. Further iterations in the solution can then account accurately for the $(ln\rho)$ contributions.

Approach II—The above system of equations becomes a linear set when the $ln\rho$ and $\rho$ terms for each point P are temporarily considered to be independent unknowns within the inspected object, thus doubling the number of unknowns. But all of them can be numerically determined from the linear algebraic equation system when another set of JQ independent measured information is utilized. That set consists of the measured flux of scattered gammas and their κ-values for points along the system's boundary. Then, it is easy to calculate values of local ρ and their logarithmic values. When the consistency of such calculated values is checked, any discrepancies can be reduced by iteration, or use of the least squares method.

Approach III—Analogous to Approach II, instead of increasing the number of equations, the number of unknowns could be reduced, omitting every other density. This is equivalent to a density value expressed as the average value of two adjacent densities. In that way, the number of equations and unknowns will be matched. If needed, iterations based on such calculated local densities can improve the accuracy of the results.

Approach IV—Another solution approach is to normalize Eq. 17 so that each density term is replaced by a density ratio close to unity. Then, the logarithmic term in Eq. 18 may be expressed by a Taylor Series, so that a non-linear, but algebraic system of equations remains to be solved. This approach requires less computing time than for the case of an equation system that incorporates both logarithmic and algebraic terms. Further, iterations may be performed to increase the accuracy of the results.

Measurement of Density Distributions of Multiple Materials in an Object

The invention may be used to determine the three-dimensional density distribution of individual multiple materials in an inspected object by adding a multiple number of gamma source energies, or positioning the detector or gamma source in a multiple number of different positions, or a combination of those alternatives. An illustration of how this is accomplished is provided below.

Consider an object made of two materials (U=2) having different densities $\rho_A$ and $\rho_B$, distributed in an unknown manner throughout the inspected object. It is recognized that the composite density at any point in the object is the sum of the component densities $\rho_A$ and $\rho_B$. Using the invention as described earlier, the object is irradiated by a gamma source having two different energies, $E_1$ and $E_2$. The invention is operated as described earlier, and data is recorded separately for irradiations by each of the gamma fluxes having photon energies at $E_1$ and $E_2$. The analysis of the two sets of data is conducted as before, up to Eq. 18. This equation is then written to incorporate the sum of two density fields, reflecting contributions of the two densities, as shown in Eqs. 20 and 21 below, where subscripts 1 and 2, with $\kappa$, k, and k' pertaining to the two cited source energies.

$$\ln \chi_1(j^*, q, U=2) = \ln[\rho_A(j^*, q) + \rho_B(j^*, q)] - \left\{ \left[\sum_{j_S}^{j^*} k_{oA}\rho_A(j,q) + k_{oB}\rho_2(j,q)\right]\Delta r + \left[\sum_{j_D}^{j^*-1} k_{1A}\rho_A(j',q') + k_{1B}\rho_B(j',q')\right]\Delta h \right\} \quad \text{Eq. 20}$$

and $$\ln \chi_2(j^*, q, U=2) = \ln[\rho_A(j^*q) + \rho_B(j^*, q)] - \left\{ \left[\sum_{j_S}^{j^*} k_{oA}\rho_A(j_1,q) + k_{oB}\rho_B(j,q)\right]\Delta r + \left[\sum_{j_D}^{j^*-1} k_{2A}\rho_A(j',q') + k_{2B}\rho_B(j',q')\right]\Delta h \right\} \quad \text{Eq. 21}$$

Since for U=2 materials (components) in the inspected object, one has available 2JN values of the parameter $\kappa$, the same number of equations of the above type can be formed. That number of equations is equal to the number of unknown local densities (JN for substance #A, and JN for substance #B), assuring the system's ability to solve for the two sets of unknown densities.

This example may be extended to a multiple number of source energies $U_{SE}$, a multiple number of source locations $U_{SL}$, and a multiple number of detector locations $U_{DL}$. Since two or more sources of different energy may be placed at the same location, the number of source locations $U_{SL}$ is always less than or equal to the number of source energies $U_{SE}$. Using the number $U_S$ to incorporate all the source-related variations (of location and energy) the product $(U_S \cdot U_{DL})$ indicates the number of equations available for solution, and also corresponds to the maximum number of unknown densities for which a solution may be obtained.

Accordingly, the invention may employ either $U_{DL}$ detectors, each of which is at a distinct location, and/or $U_{SE}$ gamma sources of the same energy, each of which are at a distinct location. One location may be selected to house multiple sources of different energies. In such a case, these sources (albeit at one location) are counted as separate items within the parameter $U_S$. Also within that number are counted all the different locations where sources of any energy might be placed. Thus, the variation in source energies is equivalent and additive to the variation in source locations, making $U_S$ a combined number of source locations and energies. Therefore, the total number of source locations $U_S$ can be equal to or smaller than $U_{SE}$. The required number of modulating units (situated either in front of the detector or in front of the source) is equal to the smaller of the two parameters $U_{SL}$ and $U_{SE}$.

Alternate Applications of the Modulating Unit

Further, in an alternate embodiment of the invention, the modulating unit may be configured in a three-dimensional geometrical arrangement, that can be serial—encoding the same streams of radiation in a serial manner—or they can be separate, e.g., one modulating unit encoding source radiation and the second modulating unit encoding the radiation immediately before it reaches the detector. In any of these, as well as other designs and applications of multiple modulation units, each of the modulating units includes its own particular set of attenuators, and may operate either independently or synchronously with the other modulation units.

Apart from the applications discussed earlier in this document, the modulating unit may be used in conjunction with any other gamma flux measurement in which it is desired to image the object from which the gammas emanate. The modulating unit may be inserted in the path of the gammas, between the inspected object and the detector, to encode the cross-section of the gamma flux with a unique periodic oscillatory attenuation in each of the nodal windows. This encoding provides a tag indicating the origin of each gamma photon within a two-dimensional cross-section of the inspected object. Depending on the design of the measurement system, this may be converted to yield three-dimensional spatial information within the object by using some form of scanning of the gamma source or the detector.

Summary

The invention described here enables a determination of the three-dimensional density distribution within an inspected object. The invention consists of three key components: a source of mono-energetic gamma radiation, a modulator, and a detector in the form of a gamma spectrometer. The invention may operate under several simple modes of operation. One such mode is the use of the device without any required relative motion between the source, modulator detector, and the inspected object (all these components may be stationary, with fixed orientation). The invention may be applied to inspect any kind of material contained in the inspected object. The device may be configured so that for one substance predominant within the inspected object, only one source and one detector need be used in the invention. Benefits from use of additional components (additional sources, modulators, or detectors) are discussed. This compact inspection system may be a fully mobile unit and is flexible regarding its positioning with respect to the inspected object. Only moderate operator/technical skills and training are required to operate the device. Another beneficial feature of the invention is that the measurements can be rapidly performed because the data processing may be conducted on-line to provide immediate results of inspection of the entire inspected object. The resolution of the reconstructed images can be varied remotely by computer control, without the need to reposition or adjust hardware components.

Potential applications of the invention include, but are not limited to: 1) screening and inspections of baggage and packages at airports for the presence of contraband; 2) detection of land mines; 3) medical diagnostic imaging; and 4) a variety of industrial applications such as monitoring of material in pipes and other uses.

One having ordinary skill in the art will understand that a computer device and software may be configured to perform the above-described analysis. Accordingly, one will understand that the various configurations described herein are merely exemplary. Accordingly, although the invention has been described based upon these preferred embodiments, it would be apparent to those skilled in the art that certain modifications, variations, and alternative constructions would be apparent, while remaining within the spirit and scope of the invention. In order to determine the metes and bounds of the invention, therefore, reference should be made to the appended claims.

LIST OF NOTATIONS, FIGURE SYMBOLS, AND ACRONYMS

Figure Symbols and Acronyms are Indented a Subscript for average (mean) values.
$a_q(t)=a(q, t)$ Trigonometric modulating gamma-attenuation function introduced by Eq. 5; it is imposed upon passing gamma fluxes by the periodic motion of attenuator elements within the modulating unit (MU).
$A_q$ Amplitude of the modulating function $a(q, t)$, on the basis of which A' and A" are specified.
$A_q'$ and $A_q"$ Amplitudes of the sine and cosine terms (respectively) of the modulating function $a(q, t)$.
$A_D$ Sensitive area of the detector (oriented toward the inspected object).
$A^*$ Area perpendicular to direction of gamma propagation.
$A_W$ Unobstructed area of the nodal window for gamma transmission through it.
AM Amplitude modulation (one of three basic kinds of modulation)
$b_n(t)=b(n, t)$ Electronically generated trigonometric function defined by Eq. 9 acting as indicated in Step 7 of the Operational Diagram, FIG. 10.
$B_n'$, $B_n"$ Amplitudes of the sine and cosine terms (respectively) of the electronic function $b(n, t)$.
$B^*$ Shift coefficient of the $b(n, t)$ function.
c Speed of light in vacuum.
C Constant.
$C_{nq}$ Product-and-sum coefficients, defined by Eq. 14.
CAT Computer Assisted Tomography.
D The photon (gammas, X-rays, or light) detector/spectrometer.
$D=\Sigma D'+\Phi'$ Detector count rate (per second, per energy bin); it is explained by Eq. 7; also, subscript pertaining to the detector, D.
$e=2.718282\ldots$, the base of natural logarithms. When raised to the power of a number, it is expressed by: exp(number).
$E_o$ Energy of gammas emitted by the radioactive source.
$E_e=mc^2$ Energy-equivalent of the relativistic rest-mass of an electron.
E' Energy of single-scattered gammas (the energy E' is associated with gamma photons scattered through an angle $\theta_j$.

$\Delta E'$ or $\Delta E_j'$ Finite-difference interval of scattered-gamma energies, with E' or $E_j'$ in the center of the respective energy interval.
$f$, F Function symbols (general).
FM Frequency modulation (one of three basic kinds of modulation)
$G^*$ Geometry parameter, introduced in Eq. 2.
h Axis oriented from any scattering point towards the detector, and the distance measured along that axis.
H Value of distance h, measured from the scattering point up to the inspected object's inner wall surface, that is close to the detector.
$H^*$ The distance along the h-axis, from the scattering point (in the center of a voxel) up to the point (or area $A^*$) where the scattered flux or its stream is defined (Usually at or close to $A_D$).
i Positive integer, representing the subscript used along the x-axis.
$i^*$ Positive integer, specifying the frequency of modulation in the $i^{th}$ group of nodal windows (that group can be a column in the rectangular modulating unit); $i^*$ is specified as a function of i, denoted by $i^*=f_i(i)$, analogous to $n^*$, defined in the group of Eqs. 10.
I $i_{max}$.
IO Inspected object.
j Positive integer, representing the subscript (index) that varies along the y-axis, observed when using the notation $y_j$. Therefore, the index j also denotes the isogonic surface, shell and slice associated with energy $E_j'$ and intersecting the y-axis. Consistent with that application, j is also used as the subscript with the energy $E_j'$, both pertaining to the flux of gammas, scattered once at an angle $\theta_j$.
J $j_{max}$
k Positive integer, representing the nodal window subscript, used along z-axis.
$k_o$, k' Gamma energy and material-dependent gamma-flux attenuation coefficients (of the original and single-scattered gammas, respectively).
K $k_{max}$.
$K^*$ Klein-Nishina scattering probability, a property that depends on source-energy and scattering angle; it is expressed as the reaction area per electron and per unit solid angle.
L Axis connecting the source and the detector (S and D, respectively).
L' Distance between D and modulating unit (or between S and modulating unit).
$L^*$ Distance between D and S.
LAE Linear algebraic equation.
$m_e$ Mass of an electron.
min, max Subscripts for minimum and maximum, respectively.
M Subscript pertaining to the modulating unit.
MCA Multi-channel pulse height analyzer. It sorts detected gamma signals into J electronic pulse-height bins according to their energy $E_j$.
MRI Magnetic resonance imaging.
MU Modulating unit.
n Positive integer, used as a subscript indicating the number of the calculational run in data processing.
$n^*$ Positive integer, specifying the frequency of the $b(n, t)$ function; it is specified in the group of Eqs. 10 as a function either of i, or of n [such as $n^*=f_n(n)$]; $n^*$ can also depend on q.
N $n_{max}=q_{max}=IK$.
NW Nodal window; as stipulated with modulating unit, N nodal windows—together with their associated attenuator elements—form the gamma-fluxes' processing system of the modulating unit. Nodal windows might or might not have physical frames defining them (if without frames, they are geometrically defined virtual windows).

o Subscript pertaining to original or specific state, conditions, or position; for example, it is used with E and k for gammas before they undergo scattering.

p Angular phase, corresponding to the time-delay (p'=p/ω), used with functions a(q, t) and b(n, t).

P Subscript pertaining to the point in space where scattering of gammas occurs (at the scattering point (SP).

$P_o$, P' Probabilities for non-attenuation of the gammas; they pertain to the original (primary) gammas, and single-scattered (secondary) gammas, respectively, discussed with Eq. 3.

P'" Non-attenuation probability of gammas, encompassing their transmission through all the wall(s) of the inspected object; P'" can be expressed by a modified Eq. 3.

P*=(1-P'), attenuation probability for scattered gammas.

PET Positron-electron emission tomography.

PM Phase modulation (one of three basic kinds of modulation).

q=(i-1)K+k a positive integer used as a subscript; it is related to both axes of the modulating unit cross-section (active area) and encompasses by one number the indexes for two axes, and thus identifies by one number any of the N nodal windows of the modulating unit and, consequently, any of the N voxels on a virtual slice. The symbol q can replace the symbols i and k, the individual subscripts of coordinates x and z, respectively, which are associated with the particular nodes located across the active area of the modulating unit q* Positive integer specifying the frequency of modulation; it is specified in Eq. 10a as a function of q, i.e., $f_q(q)=q^*$.

Q* Time-independent strength of a photon source, including light and gammas (in photons per second).

r Axis oriented from the gamma source (S) toward any scattering point (SP), and any distance measured along that axis.

r* Radial axis of a polar modulating unit (as seen in FIGS. 7 and 8).

R Specific values of the distance r, measured from the inspected object's inner wall surface at the source up to any scattering point.

R* Value of the entire distance along the r-axis, from the scattering point (in the center of a voxel) up to the source.

s Stream of gammas, defined as the product of the gamma flux and the area onto which the gammas arrive.

S As a subscript, it pertains to the source.

S Source of photons (gammas or X-radiation), or the source's center;.

S* Shift coefficient of the modulating function a(q, t).

SP Scattering point where single scattering of gammas occurs; it is associated with a voxel (a small, finite size volume around that point); a plurality of voxels form the volume of a virtual slice, and a plurality of such slices is placed within the inspected object boundaries in order to fill the inspected object.

t Time, and subscript for total.

T Half-cycle duration of a trigonometric function. During the time interval T, the slowest attenuating element within the modulating unit completes ½ of its full cycle. The convenient measurement and integration time interval is (2T).

$T_t$ Actual (total) measurement time; it is either equal to (2T) or the product of T with a positive integer, preferably an even number.

V Volume.

$\Delta V_P$ Small, but finite-size (incremental) volume, also referred to as scattering volume, or voxel, having the point SP in its center.

x, z Axes perpendicular to each other, defining modulating unit's active (operating) area and distances across it in the rectangular configuration; these two axes also serve the same purposes on the areas projected by the modulating unit upon the virtual isogonic slices (the latter areas are generally curved, due to the shape of the slices).

y Axis along which gammas travel from the radioactive source (if the modulating unit is located close to the source), entering into the inspected object; or the axis along the path gammas travel between the inspected object and the detector (if the modulating unit is located close to the detector), measured from the detector through the modulating unit, to the inspected object. This y-axis differs from the h-axis because the h-axis originates at the scattering point and can only be directed toward the detector.

$y_j$ The value of the coordinate y at the intersection of the y-axis with an isogonic virtual slice (which is a portion of the event-space that produces and radiates scattered photons of energy $E_j'$).

$y_o$ Special case of the y-axis passing through S (or D), the geometric center of the modulating unit, and close to the volumetric center of the inspected object (so that the centers of all the considered virtual slices would be aligned in a concentric manner along such an axis). Alternatively, the $y_o$ axis could extend from the modulating unit's center towards the portion of the inspected object's outer surface that is closest to the modulating unit (Again, S or D would be placed at the other end of such an axis).

$y_q$ Axis extended in the general direction explained with y, with $y_q$ passing through the center of the $q^{th}$ nodal window within the modulating unit.

z Explained with x. Additionally, in the polar modulating unit, z=r*β.

Δz Symbol used to denote physical dimensions, which are z-axis intervals within a rectangular modulating unit; this symbol is used with various superscripts (', ", Greek Letters α Angle of incidence of a directional photon (gamma) flux upon the modulating unit's nodal window, or the detector window; that angle is zero when gammas arrive perpendicular to the window.

β Angular coordinate in the polar configuration of the modulating unit, shown in FIGS. 7 and 8.

Δ Used as a prefix of a symbol, indicating its interval or increment (such as Δx, Δz, and Δβ).

χ Scattering group, defined by Eq. 5.

λ Circular frequency of the b(n, t) function, defined in Eqs. 9 and 10b.

$\phi_{jq}$ Non-modulated local flux of single-scattered gammas of a particular scattered energy ($E_j'$) as an average bin value incident upon a specific ($q^{th}$) nodal window (NW) of the modulating unit (MU), when it is located at the detector, D; Eq. 2 provides its analytical expression (a minor modification is required if the modulating unit is placed at the source, S).

$\Phi_{jq}$ Detector response to gamma streams incident upon a nodal window, as used in Eq. 6b.

Φ-hd j' Detector response to random and non-modulated gamma fluxes, as used in Eq. 7.

ρ Electron density in the matter within the inspected object.

σ Symbol defined by Eq. 13a, describing the Fourier Transform of an energy bin's count rate (which is a quantitatively known function of time).
Σ Summation symbol.
θ Gammas' scattering angle (illustrated in FIGS. 1, 2, and 9).
θ* Electron recoil angle, appearing in Compton scattering of gammas (shown in FIG. 2).
η Detector efficiency.
ω Circular frequency of the a(q, t) function, addressed in Eqs. 5 and 10a.

The invention claimed is:

1. A three-dimensional image-generating device comprising:
an external gamma radiation source configured to irradiate an inspected object with source gamma rays to generate a three-dimensional representation of said inspected object;
a modulating unit employing time-dependent nodal windows, each of said nodal windows configured to impose a different time modulation to encode gamma flux from said external gamma radiation source or Compton-scattered gamma rays from within the inspected object as at least one of said source gamma rays and said Compton-scattered gamma rays interact within said inspected object;
said modulating unit configured to identify scattering locations, by either modulating said source gamma rays or said Compton-scattered gamma rays as either said source gamma rays or said Compton-scattered gamma rays pass through said nodal windows of said modulating unit; and
a radiation detector configured to detect said Compton-scattered gamma rays scattered from within said inspected object.

2. The device as recited in claim 1, wherein said three-dimensional representation is generated by reconstructing a volumetric density distribution within said inspected object.

3. The device as recited in claim 1, wherein said external gamma radiation source, said modulating unit, and said radiation detector are stationary, having a fixed orientation.

4. The device as recited in claim 1, wherein said external gamma radiation source, said modulating unit, and said radiation detector are positioned based on a pre-selected region surrounding said inspected object.

5. The device as recited in claim 4, wherein said modulating unit is positioned either between said inspected object and said radiation detector or between said external gamma radiation source and said inspected object.

6. The device as recited in claim 4, wherein said modulating unit comprises an array of nodal windows, each having unique attenuating elements; and
said modulating unit is configured to provide identification of scattering locations as said source gamma rays or said Compton-scattered gamma rays pass through said nodal windows by a type of movement of said attenuating elements of said nodal windows, wherein said type of movement of said attenuating element is dependent upon a configuration of said modulating unit.

7. The device as recited in claim 5, wherein said modulating unit encodes a selected cross-sectional area of the gamma flux with a time-dependent oscillatory attenuation.

8. The device as recited in claim 7, wherein said modulating unit comprises a rectangular-shaped unit.

9. The device as recited in claim 7, wherein said modulating unit comprises a circular-shaped unit.

10. The device as recited in claim 1, wherein said radiation detector comprises a gamma spectrometer and approximates a point detector; and
wherein said gamma spectrometer is configured to register a plurality of single detection events of said Compton-scattered gamma rays, wherein said plurality of single detection events are detected individually; and
wherein said gamma spectrometer is configured to concurrently measure energies of Compton-scattered gamma photons associated with said detection events.

11. The device as recited in claim 10, further comprising:
a multi-channel pulse height analyzer coupled to said gamma spectrometer and configured to analyze voltage pulse heights representing the energies of the Compton-scattered gamma photons and sort the voltage pulse heights based upon the energies of the Compton-scattered gamma photons.

12. The device as recited in claim 11, wherein said gamma spectrometer and the multi-channel pulse-height analyzer are configured to determine a bin-average value of energy for said Compton-scattered gamma rays having a predetermined energy bin width.

13. The device as recited in claim 10, wherein said gamma spectrometer is configured to determine values of the gamma count rate for said Compton-scattered gamma rays arriving at the detector, wherein predetermined energy bin widths are established for counted gamma rays.

14. The device as recited in claim 1, wherein said modulating unit comprises a planar array of nodal windows.

15. The device as recited in claim 14, wherein each nodal window of said planar array of nodal windows is configured to impart a time-varying attenuation on each segment of the said gamma flux as said each segment of said gamma flux passes through said each nodal window.

16. The device as recited in claim 15, wherein each said nodal window comprises an attenuating element for performing a time-dependent gamma attenuation;
wherein said each attenuating element is configured to impose a time-dependent oscillatory attenuation of said each segment of said gamma flux as said gamma flux passes through said attenuating element of said modulating unit; and
wherein said attenuating element is mounted on a vertical shaft within a frame of said modulating unit and wherein said attenuating element is capable of oscillatory movement in a direction perpendicular to incident gammas.

17. The device as recited in claim 16, wherein a variation of intensity of said gamma flux passing through said nodal windows is accomplished by movement of said each attenuating element, and said movement is based on at least one of a selected temporal modulation and a configuration of the modulation unit.

18. The device as recited in claim 1, wherein said modulating unit encodes said Compton-scattered gamma rays to enable identification of a location of a point of scattering from within a voxel where scattering occurs from among a plurality of individual voxels contained within said inspected object.

19. The device as recited in claim 18, wherein said modulating unit includes a plurality of nodal windows containing a plurality of periodically-oscillating gamma attenuators arranged to form a matrix configuration, and wherein said each gamma attenuator oscillates with a different time-varying attenuation function.

20. The device as recited in claim 19, wherein said each different time-varying attenuation function is unique.

21. The device as recited in claim 1, wherein said external gamma radiation source comprises a mono-energetic gamma source.

22. The device as recited in claim 21, wherein said external gamma radiation source is selected from the group consisting of cesium-137 or sodium-22.

23. The device as recited in claim 1, further comprising:
a radiation shield configured to house said external gamma radiation source, wherein said radiation shield includes an opening to allow said external gamma radiation source to project said gamma rays outwardly in a direction capable of irradiating said inspected object.

24. The device as recited in claim 1, wherein said external gamma radiation source comprises a source of selected strength based upon a gamma signal strength required to interact with the radiation detector, following scattering in the inspected object.

25. The device as recited in claim 24, wherein said image-generating device includes a modulator comprising a plurality of nodal windows.

26. The device as recited in claim 24, wherein said image-generating device utilizes a plurality of voxels within the inspected object.

27. A measurement system comprising:
a modulating unit configured to receive source gamma rays or Compton-scattered gamma rays from within an inspected object irradiated by mono-energetic gamma rays from an external gamma radiation source and to modulate gamma fluxes of said source gamma rays or Compton-scattered gamma rays with a periodic function of time;
said modulation unit configured to implement an encoding process, wherein said encoding process tags a plurality of solid angle segments of said Compton-scattered or source gamma fluxes individually with different tags; and
said modulation unit comprises nodal windows, wherein each nodal window is configured to impose a different time modulation to encode said gamma fluxes, wherein said encoded Compton-scattered or source gamma fluxes are used in combination with a scattering process defined by a Compton energy-angle relationship to determine a three-dimensional distribution of local Compton-scattered gamma fluxes within said inspected object.

28. The measurement system as recited in claim 27, wherein said periodic function comprises a time-variant function for varying attenuation of said Compton-scattered or said source gamma fluxes.

29. The measurement system as recited in claim 27, wherein said encoding process aids in determining a two-dimensional mass distribution within said inspected object.

30. A measurement system comprising:
a measuring device configured to apply a Compton scattering process to an analysis of gamma rays scattered from an inspected object, wherein the gamma rays are irradiated from an external gamma radiation source;
wherein scattering points or a plurality of voxels of said Compton-scattered gamma rays having identical energies form an isogonic surface; and
a modulating unit comprising nodal windows, wherein each nodal window imposes a different time modulation for encoding a two-dimensional cross-section of source gamma fluxes or Compton-scattered gamma fluxes.

31. The measurement system as recited in claim 30, wherein said isogonic surface within the inspected object is represented by a thin layer isogonic shell having a thickness related to a spatial resolution of the measurement system.

32. The measurement system as recited in claim 31, wherein an isogonic slice comprises only a portion of said isogonic shell within the inspected object.

33. The measurement system as recited in claim 32, further comprising:
a multi-channel analyzer configured to sort voltage pulse heights associated with detected gamma rays according to a plurality of energies to determine the Compton-scattered gamma fluxes associated with scattering from said plurality of voxels contained within said isogonic slice.

34. A three-dimensional density image generating system comprising:
a modulating unit comprising nodal windows;
said modulating unit configured to receive source gamma rays or Compton-scattered gamma rays from within an inspected object irradiated by gamma rays from an external gamma radiation source, such that each nodal window imposes a different time modulation to modulate gamma fluxes of said source gamma rays or Compton-scattered gamma rays and configured to encode cross-sectional portions of source gamma fluxes or Compton single-scattered gamma fluxes to locate a first coordinate and a second coordinate of scattering points or voxels within said inspected object;
a measuring device configured to identify and separate said source gamma fluxes or said Compton single-scattered gamma fluxes originating from a plurality of voxels present in isogonic slices within the inspected object, and configured to provide a determination of a third coordinate of the scattering points within the inspected object;
wherein said measuring device is configured to determine a spatial distribution of said Compton single-scattered gamma fluxes; and
wherein said Compton single-scattered gamma flux determination includes a multitude of gamma fluxes of said gamma rays arriving from isogonic slices internal to said inspected object, wherein the isogonic slices comprise portions of isogonic shells within said inspected object.

35. A non-invasive three-dimensional density distribution measuring device comprising:
an external isotopic source configured to irradiate an inspected object with gamma rays to generate Compton single-scattered gamma photons, wherein said Compton single-scattered gamma photons obey principles of Compton scattering law;
a modulator comprising nodal windows, wherein each nodal window imposes a different time modulation to encode a periodic time-dependent oscillation distributed over a two-dimensional area of a source gamma flux or a Compton single-scattered gamma flux, whereas the source gamma flux comprises a plurality of source gamma photons and the Compton single-scattered gamma flux comprises a plurality of said Compton single-scattered gamma photons;
a spectrometer configured to detect energies and intensities of said Compton single-scattered gamma photons; and
a multi-channel pulse-height analyzer configured to sort detected gamma signals according to the energies of the detected gamma photons.

36. The device as recited in claim 35, wherein said Compton single-scattered gamma photons originate from scattering points or voxels located in a virtual isogonic shell, associated with a virtual isogonic surface of said virtual isogonic shell; and wherein said Compton single-scattered gamma photons originating from identical isogonic surfaces have identical energies.

37. The device as recited in claim 36, wherein said isogonic surface is generated by rotating an isogonic curve about a source-detector connecting line.

38. The device as recited in claim 37, wherein said virtual isogonic surfaces comprise a plurality of configurations of rotary surfaces comprising at least one of pointed poles, a sphere, and a dual curvature rotary surface having indented poles, wherein said plurality of configurations depends on Compton scattering angles of the gammas photons.

39. An inspection device comprising:
an external mono-energetic gamma radiation source configured to irradiate an inspected object with gamma photons;
a gamma photon detection unit configured to detect Compton-scattered gamma photons emanating from said inspected object;
a modulation unit configured to encode source gammas, or Compton-scattered gammas emanating from the inspected object, enroute toward the gamma photon detection unit;
a time-varying modulation unit comprising nodal windows, wherein each nodal window imposes a different time modulation to modulate said source gammas or Compton-scattered gammas with a time-variation character of flux attenuation;
a gamma signal sorting unit configured to sort counts of said detected Compton-scattered gamma photons into various energy bins;
a signal splitting unit configured to split detector output signals from each of said energy bins into multiple equal components;
an electronic function generator unit configured to generate digital signals having time-dependent functions;
a multiplication unit configured to multiply said digital signals with said detector output signals to form a combined product-function signal;
an integration unit configured to integrate, over time, said combined product-function signal to yield a plurality of linear algebraic equations;
an equation-solving unit configured to solve said plurality of linear algebraic equations to produce a determination of local Compton-scattered gamma fluxes at points of interest inside the inspected object; and
a data processing unit configured to perform said determination of said local Compton-scattered gamma fluxes and reconstruct an image of a three-dimensional density distribution within said inspected object.

40. The device as recited in claim 39, wherein said Compton single-scattered gamma fluxes are generated by said inspected object and wherein said Compton single-scattered gamma flux generation is a result of a Compton scattering process.

41. The device as recited in claim 39, wherein said external mono-energetic gamma radiation source is approximated by a point source.

42. The device as recited in claim 41, wherein attenuators within said plurality of nodal windows are configured to oscillate individually in a different manner to encode said Compton single-scattered gamma fluxes and wherein said plurality of nodal windows comprises one attenuator for each nodal window.

43. The device as recited in claim 42, wherein said modulation unit generates a plurality of time-dependencies due to oscillation of the attenuators within said plurality of nodal windows, wherein said plurality of time-dependencies exhibit a different time-dependent function for each of said plurality of nodal windows.

44. A method of generating a three-dimensional density image, comprising:
irradiating an object with an external source of gamma photons;
observing portions of source gamma fluxes or Compton single-scattered gamma fluxes that pass through corresponding nodal windows in a modulating unit and are encoded by each nodal window imposing a different time modulation on said source gamma fluxes or Compton single-scattered gamma fluxes;
modulating each portion of said source gamma fluxes or Compton single-scattered gamma fluxes that pass through a nodal window with a different time-varying attenuation function, to generate a system of linear algebraic equations;
solving said system of linear algebraic equations to generate a result; and
storing said results on a computer readable medium.

45. The method as recited in claim 44, further comprising the steps of:
detecting individual Compton single scattered gamma photons within said Compton single-scattered gamma fluxes;
generating output signals associated with each of said detected individual Compton scattered gamma photons;
counting gamma photon signals generated from detection of said individual Compton scattered gamma photons; and
sorting the counted gamma photon signals into separate bins according to the energy of the counted photons.

46. The method as recited in claim 45, further comprising the steps of determining a volumetric distribution of the Compton single-scattered gamma fluxes within the object and imaging a corresponding volumetric density distribution within said object.

47. The method as recited in claim 45, further comprising the step of positioning the modulating unit between said object and a radiation detector.

48. The method as recited in claim 45, further comprising the step of positioning the modulating unit between said object and an external radiation source.

49. The method as recited in claim 45, further comprising the step of encoding cross-sectional portions of said source gamma fluxes or said Compton single-scattered gamma fluxes.

50. The method as recited in claim 45, further comprising the step of providing a rectangular-shaped modulating unit to modulate said source gamma fluxes or said Compton single-scattered gamma fluxes.

51. The method as recited in claim 45, further comprising the step of providing a polar modulating unit to modulate said source gamma fluxes or Compton single-scattered gamma fluxes.

52. The method as recited in claim 45, further comprising the steps of:
registering of a plurality of single detection events of said Compton single-scattered gamma fluxes;
measuring energies of Compton-scattered gammas in said detection events; and
sorting said detection events based upon said energies of said Compton-scattered gammas.

53. The method as recited in claim 52, further comprising the steps of:
analyzing heights of voltage pulses associated with said detection events to identify energies of the detected gamma photons;
applying a Compton energy-angle relationship to the identified energies of the detected gamma photons to determine a spatial origin of Compton-scattered gammas; and
measuring an intensity of components of the Compton single-scattered gamma fluxes by registering count rates of the detection events, wherein the components of the Compton single-scattered gamma fluxes represent gamma fluxes arriving at the detector from at least one of different directions and different portions of the object.

54. The method as recited in claim 52, further comprising the step of:
determining a bin-average value of energy for each energy bin for said components of the Compton single-scattered gamma flux based upon a calibration of the energy bins.

55. The method as recited in claim 49, further comprising a step of:
imparting a time-varying attenuation on said Compton single-scattered gamma fluxes to generate a variation of intensity of said Compton single-scattered gamma fluxes as said segments of said Compton single-scattered gamma fluxes pass through each corresponding said nodal window.

56. The method as recited in claim 55, further comprising a step of:
imposing a time-dependent oscillatory attenuation on said portions of said source gamma fluxes or said Compton single-scattered gamma fluxes as said Compton-scattered gamma fluxes pass through an attenuating element within said nodal window; and
wherein said attenuating element is mounted on a shaft connected to a frame of a rectangular modulating unit and wherein said attenuating element is capable of translatory movement.

57. The method as recited in claim 55, further comprising the steps of: rotating said attenuating element to vary the intensity of said gamma flux in said polar modulating units.

58. The method as recited in claim 55, further comprising the step of: encoding said portions of said source gamma fluxes or said Compton single-scattered gamma fluxes to identify a point of scattering from a voxel contained within said object.

59. The method as recited in claim 55, further comprising the step of: modulating each of said cross-sectional portions of said source gamma fluxes or said Compton single-scattered gamma fluxes passing through the modulating unit and directed towards the radiation detector, approximated by a point detector.

60. The method as recited in claim 59, further comprising the step of: encoding a cross-sectional distribution of said source gamma fluxes or said Compton single-scattered gamma fluxes to locate a first coordinate and a second coordinate of scattering points or voxels within said object.

61. The method as recited in claim 60, wherein said step of encoding generates two-dimensional coordinates indicating origins of the plurality of cross-sectional components of said Compton single-scattered gamma fluxes, identifies and separates said source gamma fluxes or said Compton single-scattered gamma fluxes originating from a plurality of voxels present in isogonic slices within the object, and provides a determination of a third coordinate of the scattering points within the object.

62. The method as recited in claim 59, wherein said step of encoding further comprises modulating said source gamma fluxes or said Compton single-scattered gamma fluxes with a periodic trigonometric function.

63. A method for imaging comprising the steps of:
irradiating an inspected object with gamma rays from an external gamma radiation source;
applying a Compton scattering process to a plurality of gamma rays scattered from within the inspected object;
defining isogonic surfaces and associated isogonic shells as loci of scattering points associated with Compton-scattered gammas scattered through identical scattering angles;
using a portion of said isogonic shell within the inspected object to form a locus of said scattering points within the inspected object, from which fluxes of said Compton single-scattered gamma photons having the same energy originate, wherein only the portion of the isogonic shell within the inspected object defines an isogonic slice;
detecting said gamma photons;
sorting signals from the detected Compton-scattered gamma photons according to a plurality of energies; and
storing said signals from the detected Compton-scattered gamma photons according to said plurality of energies on a computer readable medium.

64. The method as recited in claim 63, further comprising the step of:
analyzing said signals to determine gamma fluxes associated with voxels contained within said isogonic slices.

65. A method for generating a three-dimensional image, the method comprising the steps of:
detecting source gamma rays from an external gamma radiation source or Compton-scattered gamma rays from within an inspected object irradiated by said source gamma rays after modulating gamma fluxes of said source gamma rays or said Compton-scattered gamma rays by passing through nodal windows in a modulating unit, wherein each nodal window imposes a different time modulation on said gamma fluxes;
identifying and separating said Compton-scattered gamma fluxes originating from a plurality of scattering locations from the inspected object;
formulating a gamma flux calculation procedure, wherein said gamma flux calculation yields magnitudes of Compton single-scattered gamma fluxes arriving from a plurality of known scattering points or voxels within identified isogonic slices and substantially eliminates or reduces multiple-scattered gamma fluxes arriving from said inspected object and background fluxes; and
storing said magnitudes of said Compton single-scattered gamma fluxes on a computer readable medium.

66. A method of generating a flux distribution image, comprising the steps of:
irradiating an object with gamma rays from an external gamma source to generate Compton single-scattered gamma rays, wherein said Compton single-scattered gamma rays obey principles of Compton scattering law;
encoding source gamma flux or Compton single-scattered gamma flux;
determining energies and intensity levels of said flux of Compton single-scattered gamma rays; and
sorting said energies and measuring flux intensities of portions of the Compton single-scattered gamma flux that pass through nodal windows of a modulator, wherein each nodal window imposes a different time modulation to produce a three-dimensional representation of the local Compton single-scattered gamma flux distribution.

67. The method as recited in claim 64, further comprising the step of:
calculating the loci of said scattering points or voxels, wherein said loci comprise an isogonic surface.

68. A method of inspecting comprising the steps of:
irradiating an object with gamma rays from an external gamma source;
encoding source gamma fluxes or Compton-scattered gamma fluxes by modulating either said source gamma fluxes or said Compton-scattered gamma fluxes with a time variation character, wherein each nodal window of a modulator imposes a different time modulation on said source gamma fluxes or said Compton-scattered gamma fluxes;
detecting the Compton single-scattered gamma fluxes of Compton-scattered gamma photons transmitted from said object;
generating output voltage pulse height signals from a detector, based upon individual energies of said detected Compton-scattered gamma photons;
sorting of registered counts of the detected Compton single-scattered gamma photons into energy bins of a multi-channel analyzer, according to energies of individual detected Compton single-scattered gamma photons;
splitting the output voltage pulse height signals from the multi-channel analyzer into a plurality of equal sets;
generating electronic digital signal functions;
multiplying components of said output voltage pulse height signals from a detector with said digital signal functions to form combined product-function signals;
time-integrating said combined product-function signals to generate a value representing a term in a plurality of linear algebraic equations;
storing said plurality of linear algebraic equations for local Compton single-scattered gamma fluxes on a computer readable medium;
solving said linear algebraic equations for local Compton single-scattered gamma fluxes; and
reconstructing a mass density field of said object by converting numerical local Compton single-scattered gamma fluxes into local mass densities.

69. A modulating unit comprising:
an encoder configured to encode source gamma fluxes incident on an inspected object or scattered gamma fluxes scattered from an inspected object as gamma rays irradiated from an external source interact with said inspected object, wherein said object scatters the gamma rays; and
a spatial origin identifier configured to identify spatial origins of said scattered gamma rays as source gamma rays or Compton-scattered gamma rays pass through a modulating unit comprising a plurality of nodal windows, wherein each nodal window imposes a different time modulation on said source gamma rays or said Compton-scattered gamma rays.

70. The modulating unit as recited in claim 69, wherein said plurality of nodal windows is configured to impart a time-varying attenuation on portions of the gamma flux as said portions of said gamma flux pass through said plurality of nodal windows.

71. The modulating unit as recited in claim 70, wherein said each of said plurality of nodal windows is associated with an attenuating element for performing a time-dependent gamma attenuation;
wherein said attenuating element is configured to impose a periodic, time-dependent oscillatory attenuation on said portions of said source gamma fluxes or said Compton-scattered gamma fluxes when said source gamma fluxes or said Compton-scattered gamma fluxes pass through said attenuating element of said modulating unit; and
wherein said attenuating element is mounted on a vertical shaft within a frame of said modulating unit and wherein said attenuating element is capable of movement in a vertical or horizontal direction perpendicular to a direction of incident gamma fluxes.

72. The modulating unit as recited in claim 71, wherein said time-varying attenuation generates variation of intensity of said source gamma fluxes or Compton-scattered gamma fluxes passing through said plurality of nodal windows and wherein said variation in attenuation results from a rotational movement of said attenuating elements.

73. The modulating unit as recited in claim 72, wherein said modulating unit encodes said Compton-scattered gamma fluxes or said source gamma fluxes for enabling identification of a point of scattering from a voxel contained within said inspected object.

74. The modulating unit as recited in claim 73, wherein said modulating unit includes said plurality of nodal windows containing a plurality of periodically-oscillating gamma attenuators arranged to form a matrix configuration, and wherein said gamma attenuators oscillate with different time-dependent attenuator functions.

75. The modulating unit as recited in claim 74, wherein a first gamma attenuator of said plurality of gamma attenuators within said plurality of nodal windows is configured to periodically oscillate independently of another gamma attenuator of said plurality of gamma attenuators.

76. The modulating unit as recited in claim 75, wherein periodic oscillation of said gamma attenuators in said plurality of said nodal windows influence said Compton-scattered or said source gamma fluxes passing through said plurality of nodal windows of said modulating unit enroute towards said radiation detector.

77. The device as recited in claim 39, wherein the inspection device is configured to employ a plurality of source energies, a plurality of source locations and a plurality of detector locations.

78. The device as recited in claim 77 wherein a relocation of said external mono-energetic gamma radiation source, said gamma photon detection unit, and a change in at least one of the plurality of source energies produce a different configuration for said inspection device; and
wherein said different configuration results in a different set of solvable plurality of linear algebraic equations and provides a determination of a density distribution for a multiple number of substances.

79. The method as recited in claim 68, further comprising the step of determining a three-dimensional density distribution within the inspected object.

80. A method of determining density images inside an inspected object, the method comprising the steps of:
utilizing at least two gamma source energies at the same location, each source energy having a different energy so that a number of gamma source energies is greater than a number of source locations;

combining the number of source locations and the number of source energies to generate a total number of source configurations;

multiplying the total number of source configurations by a number of detector locations to indicate a number of independent solvable equation systems and to indicate a maximum number of substances with unknown density distributions having solvable solutions; and storing said number of independent solvable equation systems on a computer readable medium.

81. The method as recited in claim 80, further comprising the steps of:

determining multiple density fields in the inspected object comprising a number of multiple substances; and using the total number of source configurations and detector locations to determine different density distributions of said number of multiple substances, wherein said different density distributions represent different substances present within the inspected object.

82. The modulating unit as recited in claim 69, wherein the modulating unit is configured to be inserted into a path of a gamma flux, between said source of gammas and said inspected object or between said inspected object and a detector, for encoding a cross-section of the gamma flux with a unique periodic oscillatory attenuation in each of the plurality of nodal windows; and wherein said modulating unit is configured to be integrated into a measuring device to enable a three-dimensional determination of density within said inspected object.

83. The modulating unit as recited in claim 82, wherein said encoder is configured to indicate a direction of origin of each gamma photon passing through the modulating unit.

* * * * *